(12) United States Patent
Tanabe et al.

(10) Patent No.: US 9,395,357 B2
(45) Date of Patent: Jul. 19, 2016

(54) METHOD OF DETECTING SPARSE PARTICLES IN A SOLUTION USING A LIGHT-EMITTING PROBE

(71) Applicant: OLYMPUS CORPORATION, Tokyo (JP)

(72) Inventors: Tetsuya Tanabe, Tokyo (JP); Hidetaka Nakata, Hachioji (JP); Takuya Hanashi, Hachioji (JP); Kunio Hori, Chofu (JP); Kazutaka Nishikawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/746,968

(22) Filed: Jan. 22, 2013

(65) Prior Publication Data

US 2013/0122488 A1 May 16, 2013

Related U.S. Application Data

(63) Continuation of application No. PCT/JP2011/066576, filed on Jul. 21, 2011.

(30) Foreign Application Priority Data

Jul. 26, 2010 (JP) ................................. 2010-167338

(51) Int. Cl.
*G01N 21/76* (2006.01)
*G01N 33/53* (2006.01)
*G01N 5/04* (2006.01)
*G01N 15/14* (2006.01)
(Continued)

(52) U.S. Cl.
CPC .......... *G01N 33/5308* (2013.01); *C12Q 1/6818* (2013.01); *G01N 5/045* (2013.01);
(Continued)

(58) Field of Classification Search
None
See application file for complete search history.

(56) References Cited

U.S. PATENT DOCUMENTS 4,251,733 A    2/1981  Hirleman, Jr.
5,866,336 A *  2/1999  Nazarenko et al. .......... 435/6.12
(Continued)

FOREIGN PATENT DOCUMENTS

EP    1 906 172 A1    4/2008
JP    4-337446 A     11/1992
(Continued)

OTHER PUBLICATIONS

International Search Report for PCT/JP2011/066576, mailing date of Sep. 20, 2011.
(Continued)

*Primary Examiner* — Robert Xu
(74) *Attorney, Agent, or Firm* — Westerman, Hattori, Daniels & Adrian, LLP

(57) ABSTRACT

There is provided an optical analysis technique enabling the detection of the condition or characteristic of a particle to be observed contained at a low concentration or number density in a sample solution using a light-emitting probe. The inventive optical analysis technique uses an optical system capable of detecting light from a micro region in a solution, such as an optical system of a confocal microscope or a multiphoton microscope, to detect the light from the light-emitting probe having bound to a particle to be observed while moving the position of the micro region in the sample solution (while scanning the inside of the sample solution with the micro region), thereby detecting individually the particle crossing the inside of the micro region to enable the counting of the particle(s) or the acquisition of the information on the concentration or number density of the particle.

17 Claims, 15 Drawing Sheets

(51) Int. Cl.
- *G01N 21/64* (2006.01)
- *C12Q 1/68* (2006.01)
- *G02B 21/00* (2006.01)

(52) U.S. Cl.
CPC ........ *G01N15/1456* (2013.01); *G01N 21/6458* (2013.01); *G02B 21/0048* (2013.01); *G02B 21/0076* (2013.01); *G01N 2015/1486* (2013.01)

(56) References Cited

U.S. PATENT DOCUMENTS

| | | |
|---|---|---|
| 6,280,960 B1 | 8/2001 | Carr |
| 6,376,843 B1 | 4/2002 | Palo |
| 6,388,746 B1 | 5/2002 | Eriksson et al. |
| 6,388,788 B1 | 5/2002 | Harris et al. |
| 6,400,487 B1 | 6/2002 | Harris et al. |
| 6,403,338 B1 | 6/2002 | Knapp et al. |
| 6,710,871 B1 | 3/2004 | Goix |
| 6,782,297 B2 * | 8/2004 | Tabor ............................. 700/55 |
| 6,856,391 B2 | 2/2005 | Garab et al. |
| 6,927,401 B1 | 8/2005 | Palo |
| 8,284,484 B2 | 10/2012 | Hoult et al. |
| 2001/0035954 A1 | 11/2001 | Rahn et al. |
| 2002/0008211 A1 | 1/2002 | Kask |
| 2002/0036775 A1 | 3/2002 | Wolleschensky et al. |
| 2003/0036855 A1 | 2/2003 | Harris et al. |
| 2003/0218746 A1 | 11/2003 | Sampas |
| 2004/0022684 A1 | 2/2004 | Heinze et al. |
| 2004/0051051 A1 | 3/2004 | Kato et al. |
| 2004/0150880 A1 | 8/2004 | Nakata et al. |
| 2005/0260660 A1 * | 11/2005 | van Dongen et al. ............. 435/6 |
| 2006/0078998 A1 * | 4/2006 | Puskas et al. .................... 436/64 |
| 2006/0158721 A1 | 7/2006 | Nakata et al. |
| 2006/0256338 A1 | 11/2006 | Gratton et al. |
| 2007/0231808 A1 | 10/2007 | Gouda et al. |
| 2008/0052009 A1 | 2/2008 | Chiu et al. |
| 2009/0159812 A1 * | 6/2009 | Livingston ................... 250/428 |
| 2010/0033718 A1 | 2/2010 | Tanaami |
| 2010/0177190 A1 | 7/2010 | Chiang et al. |
| 2010/0202043 A1 | 8/2010 | Ujike |

FOREIGN PATENT DOCUMENTS

| | | | |
|---|---|---|---|
| JP | 2002-507762 A | 3/2002 | |
| JP | 2002-543414 A | 12/2002 | |
| JP | 2004-506192 A | 2/2004 | |
| JP | 2005-098876 A | 4/2005 | |
| JP | 2005-099662 A | 4/2005 | |
| JP | 2006-333739 A | 12/2006 | |
| JP | 2007-020565 A | 2/2007 | |
| JP | 4023523 B2 | 12/2007 | |
| JP | 2008-116440 A | 5/2008 | |
| JP | 2008-536093 A | 9/2008 | |
| JP | 2008-292371 A | 12/2008 | |
| JP | 2009-145242 A | 7/2009 | |
| JP | 2009-281831 A | 12/2009 | |
| JP | 2009-288161 A | 12/2009 | |
| JP | 2011-002415 A | 1/2011 | |
| WO | 98/16814 A1 | 4/1998 | |
| WO | 99/47963 A1 | 9/1999 | |
| WO | 00/66985 A1 | 11/2000 | |
| WO | 02/12864 A1 | 2/2002 | |
| WO | 2006/084283 A2 | 8/2006 | |
| WO | 2007/010803 A1 | 1/2007 | |
| WO | 2007/118209 A2 | 10/2007 | |
| WO | WO 2007/147159 * | 12/2007 | ............... C12Q 1/68 |
| WO | 2008/007580 A1 | 1/2008 | |
| WO | 2008/080417 A1 | 7/2008 | |
| WO | 2009/117033 A2 | 9/2009 | |

OTHER PUBLICATIONS

K. Masataka, "Single molecule protein, nucleic acid, and enzyme assays and their procedures. Single molecule detection by fluorescence correlation spectroscopy", vol. 44, No. 9, pp. 1431-1438, (1999), With English translation.

F. J. Meyers-Almes, "10 Nanoparticle Immunoassays: A new Method for Use in Molecular Diagnostics and High Throughput Pharmaceutical Screening based on Fluorescence Correlation Spectroscopy", R. Rigler, edit., Springer, Berlin, pp. 204-224, (2000).

N. Kato et al., "A single molecule analyzer that enable new analysis of DNA and protein interactions", Gene Medicine vol. 6, No. 2, pp. 271-277, (2002).

S. Sando and E.T. Kool., "Quencher as Leaving Group: Efficient Detection of DNA-Joining Reactions", J. Amer. Chem. Soc, vol. 124, No. 10, pp. 2096-2097, (2002).

Carlsson K et al: "Three-dimensional microscopy using a confocal laser scanning microscope", Optics Letters, Optical Society of America, vol. 10, No. 2, Feb. 1985, pp. 53-55, XP007922413, ISSN: 0146-9592.

International Search Report of PCT/JP2011/053483, mailing date Mar. 29, 2011.

International Search Report of PCT/JP2011/053481, mailing date Mar. 29, 2011.

Park et al., "Counting the Number of Fluorophores Labeled in Biomolecules by Observing the Fluorescence-Intensity Transient of a Single Molecule", Bulletin of the Chemical Society of Japan, vol. 78, No. 9, p. 1612-1618, Aug. 30, 2005.

U.S. Office Action mailed Apr. 2, 2013, issued in related U.S. Appl. No. 13/596,280.

P. Kask et al., "Two-Dimensional Fluorescence Intensity Distribution Analysis: Theory and Applications", Biophysical Journal, vol. 78, pp. 1703-1713, (2000).

P. Kask et al., "Fluorescence-intensity distribution analysis and its application in biomolecular detection technology", PNAS, vol. 96, No. 24, pp. 13756-13761, (1999).

Chinese Office Action dated Aug. 13, 2013, issued in related Chinese application No. 2011800116553 with translation (16 pages).

International Preliminary Report on Patentability (PCT/IPEA/409) issued in related PCT/JP2011/053483.

Chinese Office Action dated Aug. 9, 2013, issued in related Chinese application No. 201180011640.7 with translation.

International Search Report issued in related PCT/JP2011/053482, mailing date Mar. 29, 2011.

International Preliminary Report on Patentability (PCT/IPEA/409) issued in related PCT/JP2011/053482.

U.S. Office Action dated Jan. 3, 2013, issued in related U.S. Appl. No. 13/597,825.

Chinese Office Action dated Feb. 7, 2013, issued in related Chinese application No. 201180011644.5 with translation (18 pages).

Extended European search report dated Mar. 28, 2013, issued in related EP application No. 11750481.

Japan Office Action dated Dec. 18, 2012, issued in related JP application No. 2012-503060 with translation.

Written Opinion of International Searching Authority (PCT/ISA/237) issued in related PCT/JP2011/053481.

International Preliminary Report on Patentability (PCT/IPEA/409) issued in related PCT/JP2011/053481.

Goodwin et al. "Rapid sizing of individual fluorescently stained DNA fragments by flow cytometry," Nucleic Acids Research, 1993, vol. 21, No. 4 pp. 803-806.

Keller et al. "Single-Molecule Fluorescence Analysis in Solution," Applied Spectroscopy, 1996, vol. 50, No. 7, pp. 12A-32A.

Lee et al. "Laser-Induced Fluorescence Detection of a Single Molecule in a Capillary," Analytical Chemistry, Dec. 1, 1994, vol. 66, No. 23, pp. 4142-4149.

Li et al. "Ultrasensitive Coincidence Fluorescence Detection of Single DNA Molecule," Analytical Chemistry, Apr. 1, 2003, vol. 75, No. 7, pp. 1664-1670.

Nie et al. "Probing Individual Molecules with Confocal Fluorescence Microscopy," Science, Nov. 11, 1994, vol. 266, pp. 1018-1021.

Tahari, "Fluorescence Correlation Spectroscopy: Ultrasensitive Detection in Clear and Turbid Media," University of Illinois, 2005, pp. 1-88.

Wu et al. "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, pp. 2157-2159.

(56) References Cited

OTHER PUBLICATIONS

Itoh et al. "A New Method for Detection of Influenza Viruses by Single Particle-Recognition Based on the Principle of Fluorescence Correlation Spectroscopy," Chemistry and Biology, 2009, vol. 47, No. 12, pp. 823-830.
U.S. Office Action dated Oct. 4, 2013, issued in related U.S. Appl. No. 13/596,243.
Extended European Search Report dated Oct. 20, 2014, issued in related EP Application No. 12770835.2 (10 pages).
European Communication Pursuant to Article 94(3) EPC dated Nov. 20, 2014, issued in corresponding European Patent Application No. 11812369.4 (6 pages).
Shuming N. et al., "Real-Time Detection of Single Molecules in Solution by Confocal Fluorescence Microscopy", Analytical Chemistry, American Chemical Society, vol. 67, No. 17, pp. 2849-2857, (1995).
Chinese Office Action dated Jul. 14, 2014, issued in corresponding Chinese Patent Application No. 201180036710.4 (6 pages).
Chinese Office Action dated Jul. 14, 2014, issued in corresponding Chinese Patent Application No. 201180036710.4 (12 pages).
Official Notice dated May 13, 2015, issued in corresponding European application No. 11812369.4 (5 pages).
Office Action dated Mar. 25, 2015, issued in Chinese Patent Application No. 201180036710.4, with English translation (8 pages).
Office Action dated May 19, 2015, issued in corresponding Japanese Patent Application No. 2012-526460 with English translation (8 pages).
Official Notice dated Nov. 30, 2015, issued in corresponding European application No. 11812369.4.
Prasad V et al. "Topical Review; Confocal microscopy of colloids", Journal of Physics: Condensed Matter, Institute of Physics Publishing, Bristol, GB, vol. 19, No. 11, Mar. 21, 2007, p. 113102.

* cited by examiner

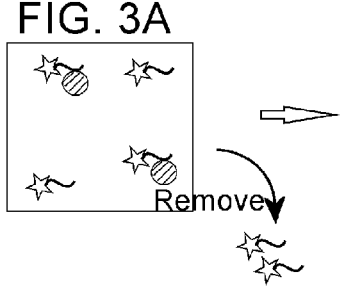
FIG. 3A
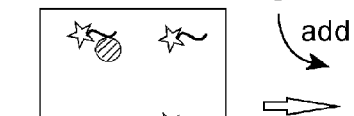
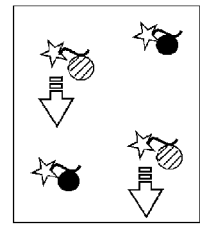
FIG. 3B
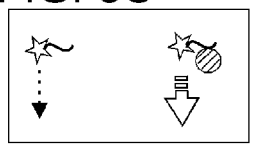
FIG. 3C
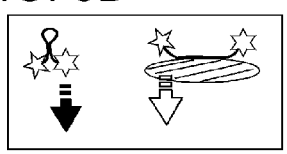
FIG. 3D
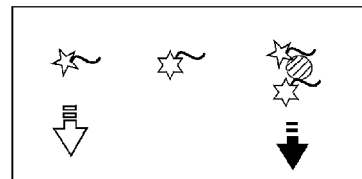
FIG. 3E
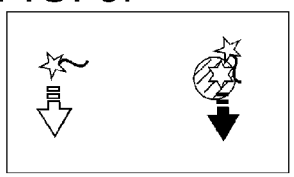
FIG. 3F
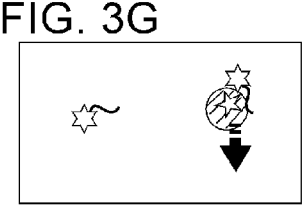
FIG. 3G
FIG. 3H
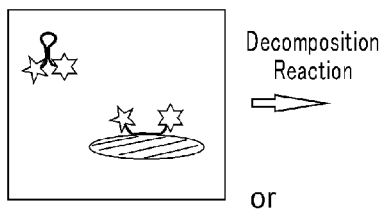
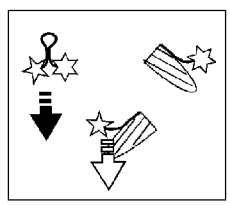
Decomposition Reaction
or
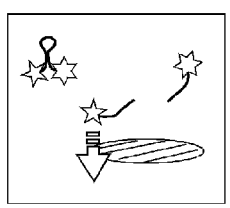
Decomposition Reaction FIG. 9A
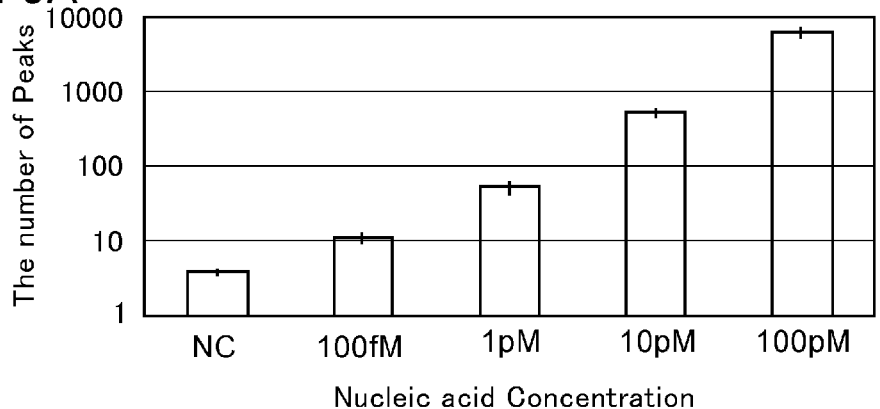
FIG. 9B
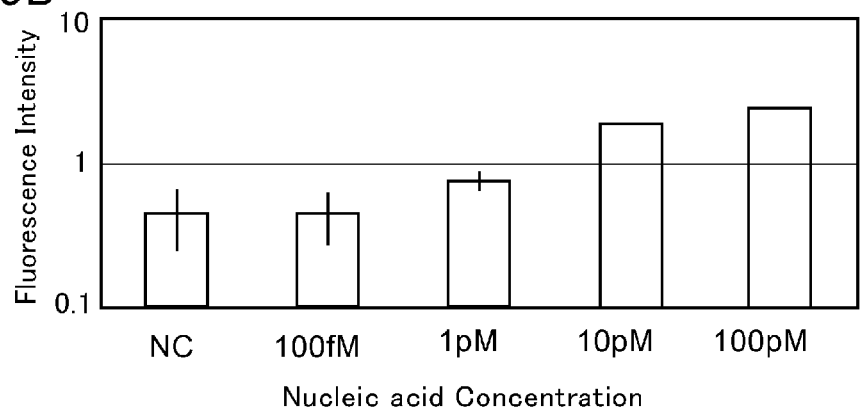
FIG. 9C  Low concentration    High concentration
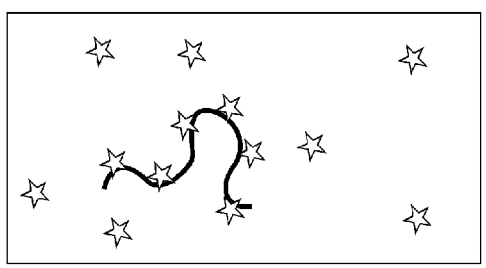 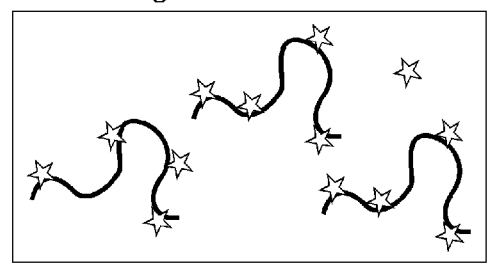

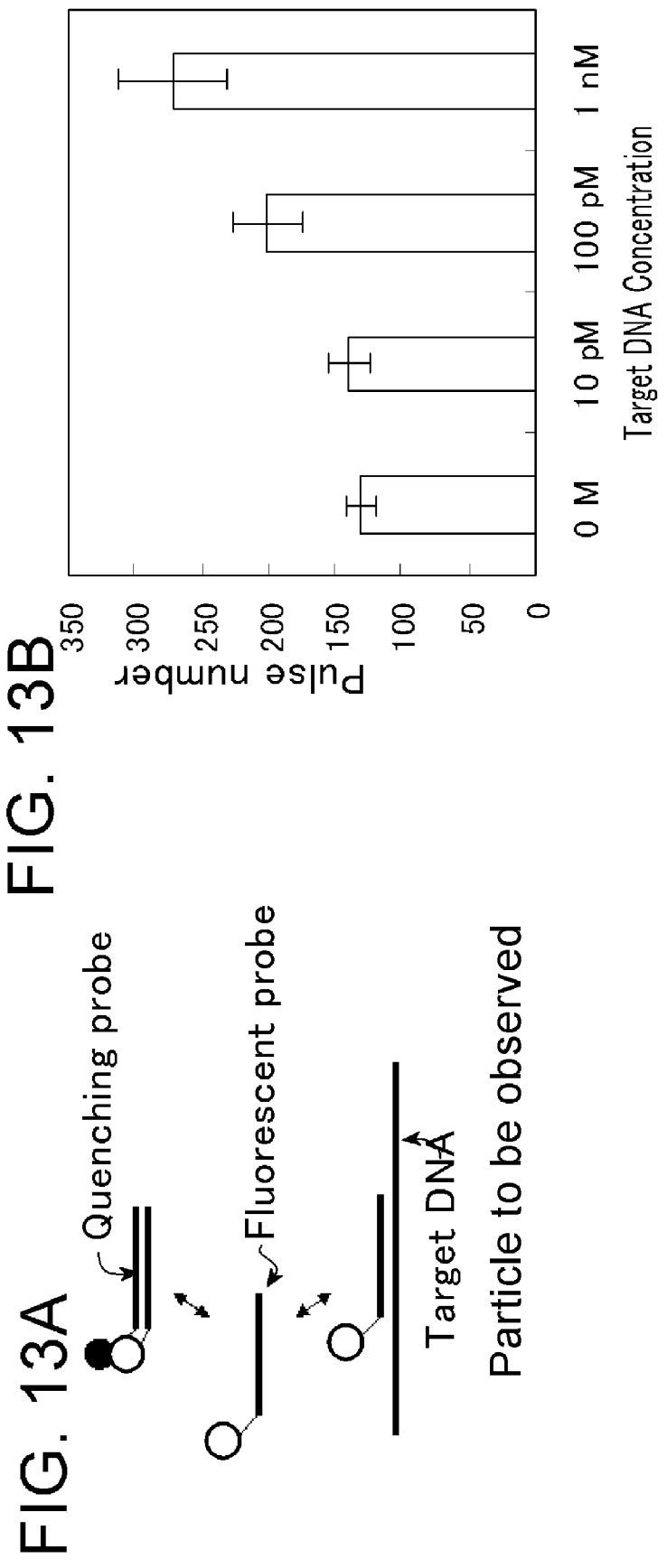

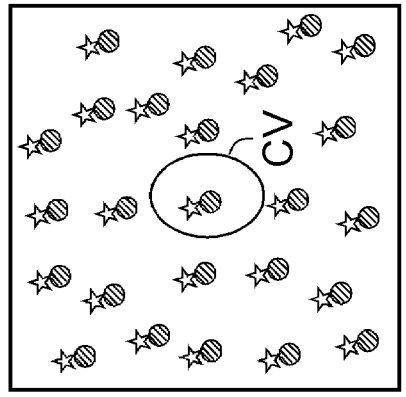
FIG. 15A High Concentration (e. g. ~ 1nM)
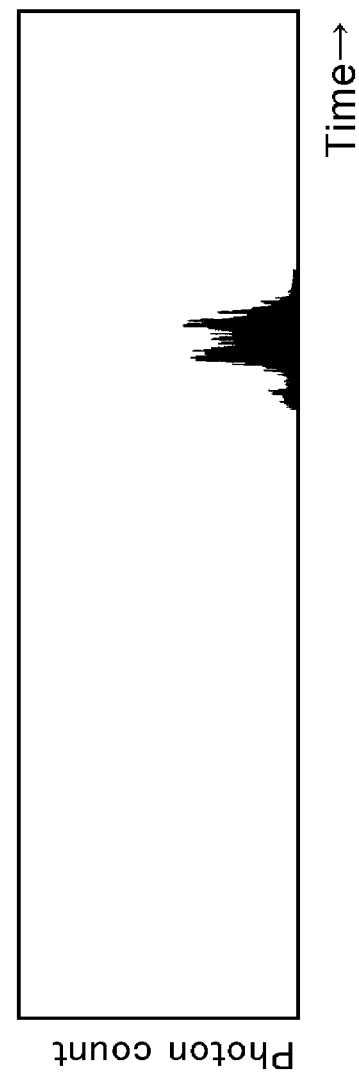
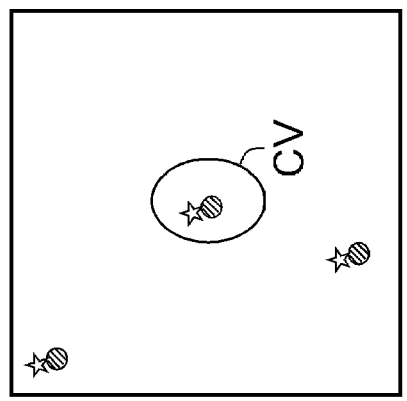
FIG. 15B Low Concentration (e. g. ~ 1pM)

METHOD OF DETECTING SPARSE PARTICLES IN A SOLUTION USING A LIGHT-EMITTING PROBE

TECHNICAL FIELD

This invention relates to an optical analysis method capable of acquiring useful information in an analysis of conditions (interaction, binding or dissociating condition, etc.) of a particulate object, e.g. an atom, a molecule or an aggregate thereof (Hereafter, these are called a "particle".) such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, and more specifically, relates to a method of performing a detection of a particulate object in a solution, a measurement of its concentration or its number density, etc. by means of a light-emitting probe. In this regard, in this specification, a "light-emitting probe" is a substance which emits light by fluorescence, phosphorescence, chemiluminescence, bioluminescence, light scattering, etc., and binds to a particle to be an observed object to enable the observation of the particle.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of intermolecular interaction, binding or dissociating reaction of biological molecules, etc. by means of such a faint light measurement technique. For example, in Fluorescence Correlation Spectroscopy (FCS, see e.g. patent documents 1 and 2 and non-patent documents 1-3), by means of the optical system of a laser confocal microscope and a photon counting technique, there is performed the measurement of fluorescence intensity of fluorescence molecules or fluorescently labeled molecules (fluorescent molecules, etc.), entering into and exiting out of a micro region in a sample solution (the focal region to which the laser light of the microscope is condensed, called a "confocal volume"), and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 3) or Photon Counting Histogram (PCH, e.g. patent document 4), there is generated a histogram of fluorescence intensity of fluorescent molecules, etc., entering into and exiting out of a confocal volume, measured similarly to FCS, and the average value of the characteristic brightness of the fluorescent molecules, etc. and the average number of molecules dwelling in the confocal volume are calculated by fitting a statistical model formula to the distribution of the histogram, so that, based on the information thereof, the structure or size change, binding or dissociative conditions or dispersion and aggregation conditions of molecules can be estimated. Moreover, in patent documents 5 and 6, there are proposed methods of detecting fluorescent substances based on a time progress of fluorescence signals of a sample solution measured using the optical system of a confocal microscope. Patent document 7 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the method employing the fluorescent light measurement technique of a micro region using the optical system of a confocal microscope and a photon counting technique, such as FCS and FIDA, a sample amount required for the measurement may be extremely small (an amount used in one measurement is at most several tens of $\mu L$), and its concentration is extremely low as compared with the prior art, and the measuring time is also shortened extremely (In one measurement, a measuring process for time of order of seconds are repeated several times). Thus, those techniques are expected to be a strong tool enabling an experiment or a test at low cost and/or quickly in comparison with conventional biochemical methods, especially in conducting an analysis of rare or expensive samples often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent No. 4023523
Patent document 4: WO 2008-080417
Patent document 5: Japanese Patent laid-open publication No. 2007-20565
Patent document 6: Japanese Patent laid-open publication No. 2008-116440
Patent document 7: Japanese Patent laid-open publication No. 4-337446 Non-patent documents
Non-patent document 1: Masataka Kaneshiro; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.
Non-patent document 3: Noriko Kato, et al. "Gene medicine", Vol. 6, No. 2, pages 271-277.
Non-patent document 4: S. Sando and E. T. Kool, J. Amer. Chem. Soc, 2002, Vol. 124, pages 2096-2097

SUMMARY OF INVENTION

Technical Problem

In the above-mentioned optical analysis techniques, such as FCS, FIDA and PCH, briefly speaking, the magnitude of time fluctuation of measured fluorescence intensity is computed by a statistical procedure, and then various characteristics of fluorescent molecules, etc., entering in and exiting out of a micro region in a sample solution, are determined based on the magnitude of the fluctuation. Thus, in order to obtain a significant result in the above-mentioned optical analysis technique, it is preferable to prepare the concentration or number density of fluorescent molecules, etc. to be the observation objects in the sample solution so that fluorescent molecules, etc. of the number enabling a statistical process will enter in and exit from a micro region in one measuring term of a length of order of seconds in an equilibrium, preferably so that about one fluorescent molecule, etc. will be always present in the micro region (Typically, since the volume of a confocal volume is about 1 fL, it is preferable that the concentration of fluorescent molecules, etc. is about 1 nM or more). In the other words, when the concentration or number density of particles to be observed in a sample solution is much lower than the level enabling a statistical process (for example, much lower than 1 nM), there would occur a condition where an object to be observed rarely enters into the micro region in the measuring term, and accordingly, the measuring result of fluorescence intensity would include a long period of a condition in which no object to be observed exists at all in the micro region and also the amount of observation of significant fluorescence intensity would decrease, and thus no significant or accurate analysis result could be expected in the optical analysis technique based on the statistical fluctuation of the fluorescence intensity as described above.

In the method of detecting fluorescent substances using the optical system of a confocal microscope described in patent documents 5 and 6, without performing the statistical process of the fluorescence intensity fluctuation as described above, the presence or absence of a fluorescent molecule, etc. to be observed in a sample can be determined from the presence or absence of generation of a fluorescence signal having a significant intensity in the measuring term over several seconds and it is disclosed that a correlation between the frequency of fluorescence signals having significant intensity and the number of the fluorescent molecules, etc. in a sample is obtained. In particular, in patent document 6, it is suggested that the generation of a random flow agitating the inside of a sample solution improves the detection sensitivity. However, even in those methods, the existences of fluorescent molecules, etc. entering into a micro region at random by diffusion or a random flow are simply detected, where the behavior of a particle of the fluorescent molecules, etc. in the micro region cannot be grasped, and therefore, for instance, the counting of particles or the quantitative computing of the concentration or number density of particles have not been achieved. Moreover, the technique described in patent document 7 is to detect individual existences of fluorescent fine particles in the flow in a flow cytometer or fluorescent fine particles fixed on a substrate, not a technique for detecting particles, such as molecules and colloids, being dissolved or dispersed in a normal condition in a sample solution, i.e. particles moving at random in a sample solution, and thus, it has not been achieved to quantitatively compute out the concentration or number density of particles dissolved or dispersed in a sample solution. Further, since the technique of patent document 7 includes processes, such as the measurement in a flow cytometer or the treatment of fixing fluorescence particles on a substrate, the sample amount necessary for the test increases substantially as compared with the cases of the optical analysis techniques, such as FCS, FIDA and PCH, and complicated and advanced operational techniques may be requested to a person conducting the test.

Then, in order to eliminate the use of the statistical procedures as performed in the optical analysis techniques, such as FCS, FIDA and PCH, thereby achieving detections of the conditions or characteristics of a particle to be observed in a sample solution in which the concentration or number density of the particle to be observed is lower than the level at which the afore-mentioned optical analysis techniques are used, Applicant of the present application has proposed an optical analysis technique of observing a particle to be observed based on a new principle in Japanese patent application No. 2010-044714 and PCT/JP2011/53481. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. a light detection region, is moved in the sample solution, namely, the inside of the sample solution is scanned with the micro region, and when a particle which emits light (called as a "light-emitting particle" in the followings), dispersed and moving at random in the sample solution, crosses the inside of a micro region, the light emitted from the light-emitting particle in the micro region is detected, and thereby each of the light-emitting particles in the sample solution is detected individually such that it becomes possible to perform the counting of light-emitting particles and the acquisition of the information about the concentration or number density of the light-emitting particle in the sample solution. According to this new optical analysis technique (called a "scanning molecule counting method", hereafter), a sample amount necessary for measurement may be small (for example, about several 10 μL) and the measuring time is short similarly to optical analysis techniques, such as FCS, FIDA and PCH, and also, it becomes possible to quantitatively detect characteristics, such as a concentration or a number density, of a light-emitting particle at a lower concentration or number density, as compared with the case of optical analysis techniques, such as FCS, FIDA and PCH.

In order to further develop the scanning molecule counting method proposed in the above-mentioned patent application No. 2010-044714, the main object of the present invention is to propose a method that advantageously employs the scanning molecule counting method especially for observing a particle dispersed and moving at random in a sample solution by means of a light-emitting probe.

Solution to Problem

According to the present invention, there is provided an optical analysis method of detecting light from a light-emitting probe binding to a particle dispersed and moving at random in a sample solution by using an optical system of a confocal microscope or a multiphoton microscope to detect the particle characterized by comprising steps of: preparing the sample solution containing the particle and the light-emitting probe; moving a position of a light detection region of the optical system in the sample solution by changing an optical path of the optical system; detecting light from the light detection region during moving the position of the light detection region in the sample solution; and detecting individually a light signal from each light-emitting probe binding to the particle in the detected light to detect the particle individually. In this structure, "a particle dispersed and moving at random in a sample solution" is a particle, such as an atom, a molecule or an aggregate of these being dispersed or dissolved in a sample solution, (which particle may be either one emitting light or one not emitting light), and it may be an arbitrary particulate matter making the Brownian motion freely in a solution without being fixed on a substrate, etc.

And, a "light-emitting probe" is a substance having a characteristic which binds to or associates with the particle to be the observed object and emits light (usually, molecules or those aggregates), and typically, it is a fluorescent particle, but may be a particle which emits light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective. In this connection, especially in a confocal microscope, this region is determined in accordance with the spatial relationship of an objective and a pinhole. For a light-emitting probe which emits light without illumination light, for example, a molecule or an aggregate thereof which emits light according to chemiluminescence or bioluminescence, no illumination light is required in the microscope. In this regard, in this specification, "a light signal" means "a signal expressing light from a light-emitting probe having bound to a particle" unless noted otherwise.

As understood from the above, in the basic structure of the invention, first, after preparing, by an arbitrary method, a sample solution in which particles to be detected and light-emitting probes binding to the particles are mixed, the detection of light is sequentially performed while the position of a light detection region is moved in the sample solution, namely, while the inside of the sample solution is scanned with the light detection region. Then, when the moving light detection region includes a randomly moving light-emitting probe having bound to or associating with a particle, the light from the light-emitting probe is detected by the light detecting portion, and thereby, the existence of one particle will be detected. (Depending on an experimental manner, it is possible that, at the time of detection of light, a light-emitting probe has been dissociated from a particle to which the light-emitting probe had bound once). And, in the sequentially detected light, a light signal from a light-emitting probe is individually detected, and thereby, the individual existences of particles (having bound to a light-emitting probe) are sequentially detected one by one, and accordingly, diverse information on the condition of the particle in the solution will be acquired. Concretely, for example, in the above-mentioned structure, the number of the particles detected during the moving of the position of the light detection region may be counted by counting the number of the individually detected particles (The Counting of particles). According to this structure, by associating the number of particles with the moving amount of the position of the light detection region, the information on the number density or concentration of the particle in the sample solution will be acquired. Especially, by determining the whole volume of the moving track of the position of the light detection region by an arbitrary method, for example, by moving the position of the light detection region at a predetermined speed, the number density or concentration of the particle can be concretely computed. Of course, instead of determining directly the absolute number density value or concentration value, the relative ratio of the number density or concentration to a plurality of sample solutions or a standard sample solution to be a reference of a concentration or a number density may be computed. Moreover, in the above-mentioned present invention, since the position of the light detection region is moved by changing the optical path of an optical system, the movement of the light detection region is quick without substantial generation of mechanical vibration and hydrodynamic effect in the sample solution, and therefore, the measurement of light can be performed under a stable condition without dynamic action affecting the particle to be detected (vibration and flow acting in a sample solution might change the properties of the particles). Further, since no structure for flowing a sample solution is required, the measurement and analysis can be conducted with a small amount of the sample solution (at the level of one to several tens of μL) similarly to FCS and FIDA, etc.

In the step of detecting a particle individually in the above-mentioned inventive method, the judgment, from the sequentially detected light signal, of whether or not a light-emitting probe having bound to one particle (including a case that one light-emitting probe has bound to one particle, a case that two or more light-emitting probes have bound to one particle and a case that a light-emitting probe which had bound to one particle has dissociated from the particle, depending upon an experiment manner; the same in the following) has entered into the light detection region may be conducted based on the shape of the light signal detected in time series. In an embodiment, typically, it may be designed such that, when a light signal having the intensity larger than a predetermined threshold value is detected, it is detected that one light-emitting probe having bound to a particle has entered into the light detection region.

Moreover, in the above-mentioned step of moving the position of the light detection region, the moving speed of the position of the light detection region in the sample solution is appropriately changed based on the characteristic or the number density or concentration of the light-emitting probe having bound to a particle in the sample solution. As understood by ones ordinarily skilled in the art, the condition of detected light from the light-emitting probe having bound to a particle may change in accordance with its characteristic, number density or concentration in a sample solution. Especially, when the moving speed of the light detection region becomes quick, the amount of light obtained from one light-emitting probe having bound to a particle will be reduced, and therefore it is preferable that the moving speed of the light detection region can be changed appropriately so that the light from one light-emitting probe having bound to a particle can be measured precisely or with sufficient sensitivity.

Furthermore, in the above-mentioned step of moving the position of the light detection region, the moving speed of the position of the light detection region in the sample solution is preferably set to be higher than the diffusional moving velocity (the average moving speed of a particle owing to the Brownian motion) of a light-emitting probe having bound to a particle to be a detected object (namely, a particle and light-emitting probe combination, or a light-emitting probe which has dissociated from a particle after having bound to the particle, depending on an experimental manner). As explained above, in the inventive method, when the light detection region passes through the position where a light-emitting probe having bound to a particle exists, the light emitted from the light-emitting probe is detected, so that the light-emitting probe will be detected individually. However, when a light-emitting probe having bound to a particle moves at random owing to the Brownian motion to move into and out of the light detection region multiple times, the light signal from one light-emitting probe having bound to a particle (showing the existence of the particle to be detected) will be detected multiple times, and therefore it would become difficult to make the existence of one particle to be detected associate with the detected light signal. Then, as described above, the moving speed of the light detection region is set higher than the diffusional moving velocity of the light-emitting probe having bound to a particle, and thereby it becomes possible to make one light-emitting probe having bound to a particle correspond to one light signal (indicating the existence of a particle). In this regard, since the diffusional moving velocity differs depending upon a light-emitting probe having bound to a particle, it is preferable that the moving speed of the light detection region can be changed appropriately according to the characteristics (especially, the diffusion constant) of the light-emitting probe having bound to a particle as described above.

The changing of the optical path of the optical system for moving the position of the light detection region may be done in an arbitrary way. For example, the position of the light detection region may be changed by changing the optical path using a galvanomirror employed in the laser scan type optical microscope. The movement track of the position of the light detection region may be set arbitrarily, for example, which is selectable from circular, elliptical, rectangular, straight and curvilinear ones.

By the way, as understood from the above-mentioned explanation, in the inventive method, the existence of a particle to be detected is found by detecting light from a light-emitting probe having bound to or associating with the particle. Thus, when a light-emitting probe which has not bound to a particle exists in a sample solution, the accuracy in the detected result of the particle would deteriorate. So, in an embodiment of the inventive method, a structure for preventing the detection of light from a light-emitting probe having not bound to a particle in a sample solution may be preferably included.

As one of such structures for preventing the detection of light from a light-emitting probe having not bound to a particle, in the step of preparing a sample solution in the inventive method, the step of separating the light-emitting probe having not bound to a particle from a sample solution may be performed. For a concrete technique for separating a light-emitting probe having not bound to a particle, there may be selected an arbitrary method of separating two or more substances physically by utilizing the difference in characteristics, for example, the difference in size or molecular weight, affinity to an arbitrary substance, electrically charged condition, etc., between a single light-emitting probe or a light-emitting probe having not bound to a particle, and a particle and light-emitting probe combination or a light-emitting probe having bound to a particle. In an embodiment of a separation technique of a single light-emitting probe or a light-emitting probe having not bound to a particle, a single light-emitting probe or a light-emitting probe having not bound to a particle may be eliminated from a sample solution by separating the single light-emitting probe or light-emitting probe having not bound to a particle from a particle and light-emitting probe combination or a light-emitting probe having bound to a particle, using an arbitrary method of operations including adsorption and extraction or washing through chromatography (hydrophilic/hydrophobic chromatography, affinity chromatography, an ion exchange chromatography, etc.), ultrafiltration, electrophoresis, phase separation, centrifugal separation, solvent extraction, filter adsorption, etc.

Moreover, for an alternative structure for preventing the detection of light from a light-emitting probe having not bound to a particle, the method may be designed such that the differentiation between a single light-emitting probe or a light-emitting probe having not bound to a particle and a particle and light-emitting probe combination or a light-emitting probe having bound to a particle becomes possible by choosing a light-emitting probe or other components in a sample solution so as to provide a difference in the light-emitting characteristics between a single light-emitting probe or a light-emitting probe having not bound to a particle and a particle and light-emitting probe combination or a light-emitting probe having bound to a particle in a sample solution, or so as to avoid the emission (from a sample solution) of light of a single light-emitting probe or a light-emitting probe having not bound to a particle. This structure is advantageous in that no operation of separating physically a single light-emitting probe or a light-emitting probe having not bound to a particle from a particle and light-emitting probe combination or a light-emitting probe having bound to a particle is required.

As one example of such a structure, in the above-mentioned inventive method, a substance whose light-emitting characteristic changes when it binds to a particle to be detected may be chosen as a light-emitting probe so that the light from the light-emitting probe having bound to a particle to be detected can be selectively detected in the step of detecting light. For example, when a particle to be detected is a nucleic acid or a nucleic acid analogue, an intercalator fluorescent dye, which exhibits increase of fluorescence intensity and/or change of fluorescence wavelength when it binds to a nucleic acid or a nucleic acid analogue, will be chosen as a light-emitting probe, and when a particle to be detected is a protein, a dye (fluorescent dyes, e.g. hydrophobic probes: ANS, MANS, TNS) whose fluorescence intensity and/or fluorescence wavelength changes owing to its peripheral environmental change when it binds to the protein will be chosen as a light-emitting probe. Or, as a light-emitting probe, there may be employed a substance, consisting of at least two components, in which fluorescence will be emitted owing to the mutual positional change of the above-mentioned at least two components when the substance binds to a particle to be detected. For examples of such a substance, there are considered a fluorescent protein which will emit strong fluorescence owing to structural change when it binds to a particular particle and a molecule which will assemble to form a fluorescent metal complex when it binds to a particular particle (a ligand of a complex). According to these structures, in any cases, a single light-emitting probe or a light-emitting probe having not bound to a particle hardly emits light, or even if it emits light, its wavelength is different from that of the particle and light-emitting probe combination, and therefore it is possible to detect selectively the light from the particle and light-emitting probe combination.

Moreover, for an alternative structure for providing a difference in the light-emitting characteristics between a single light-emitting probe or a light-emitting probe having not bound to a particle and a particle and light-emitting probe combination or a light-emitting probe having bound to a particle in a sample solution, a fluorescence energy transfer phenomenon may be used advantageously.

As such an example, for instance, in the step of preparing a sample solution, there may be conducted a step of binding a light-emitting probe having not bound to a particle with an acceptor which absorbs the light which the light-emitting probe emits. Here, the acceptor is an arbitrary substance which binds to or associates with only a single light-emitting probe or a light-emitting probe having not bound to a particle, and (immediately) absorbs the light which a light-emitting probe emits by a fluorescence energy transfer (quencher or energy acceptor). According to this structure, even when a light-emitting probe having not bound to a particle to be detected enters into the light detection region, this light-emitting probe has bound to the acceptor, and thus, it emits no light or only the light of different wavelength from that emitted from a particle and light-emitting probe combination or a light-emitting probe having bound to a particle, and thereby it becomes possible to detect only the light of a particle and light-emitting probe combination or a light-emitting probe having bound to a particle. As an example, in a case that a particle to be detected is a nucleic acid or a nucleic acid analogue and a light-emitting probe is a fluorescently labeled nucleic acid or nucleic acid analogue, when a particle and light-emitting probe combination is formed by making the particle to be detected and light-emitting probe react in a sample solution, and subsequently when a nucleic acid or nucleic acid analogue to which an acceptor for the light of the fluorescent label of the light-emitting probe has been attached is added into the sample solution, the nucleic acid or nucleic acid analogue to which the acceptor has been attached binds to the light-emitting probe which has not bound to a particle to be detected, and thereby, it becomes possible to detect selectively the light only from the particle and a light-emitting probe combination.

Further, in another example using the fluorescence energy transfer phenomenon, there may be employed, as a light-emitting probe, a substance which has an energy donor site and an energy acceptor site, producing a fluorescence energy transfer phenomenon when those are close mutually, wherein the distance between the energy donor site and energy acceptor site changes when the substance binds to a particle to be detected (Molecular beacon method, Scorpion method, etc.). In this case, since the extent of the occurrence of the fluorescence energy transfer phenomenon varies depending upon whether or not the light-emitting probe has bound to a particle to be detected, a single light-emitting probe does not emit light or the emission wavelength of a single light-emitting probe and the emission wavelength of a particle and light-emitting probe combination differ from one another, and thereby it becomes possible to detect selectively the light from the particle and light-emitting probe combination.

Further, in the other example using the fluorescence energy transfer phenomenon, for the light-emitting probe, there are prepared a first probe used for an energy donor in a fluorescence energy transfer phenomenon and a second probe used for an energy acceptor in the fluorescence energy transfer phenomenon, and those are mixed with a particle to be detected. Then, from the combination that both the first and second probes bind to the particle to form, the light of the second probe is emitted through a fluorescence energy transfer phenomenon, and thus, only the light from the combination can be selectively detected, being distinguished from the light from the first probe (In this case, the second probe having not bound to a particle hardly emits light). Or, in a case that a particle to be detected has a site which becomes an energy acceptor of the light emitted by a light-emitting probe, it may be achieved to selectively detect only the light from the particle and light-emitting probe combination by choosing a light-emitting probe which can be used as the donor and detecting the light emitted from the energy acceptor site of the particle through the fluorescence energy transfer phenomenon which occurs when the light-emitting probe binds to the particle, and further, on the contrary, in a case that a particle to be detected has a light-emitting site, it may be achieved to selectively detect only the light from the particle and light-emitting probe combination by choosing, as a light-emitting probe, a substance having a site to be an energy acceptor of the light emitted by the light-emitting site of the particle and detecting the light emitted from the light-emitting probe through the fluorescence energy transfer phenomenon which occurs when the light-emitting probe binds to the particle.

Typically, the particle detected by the inventive method may be a biological particulate object, such as a biological molecule, e.g. a protein, a peptide, a nucleic acid, a lipid, a sugar chain, an amino acid or an aggregate of these, etc., a virus or a cell, or a non-biological particle (for example, an atom, a molecule, a micelle, a metallic colloid, etc.), and the light-emitting probe may be an arbitrary substance which specifically or nonspecifically binds or adheres to a particle as described above. For instance, when the particle to be detected is a nucleic acid, the probe may be a dye molecule, a nucleic-acid binding protein, etc. that binds with a nucleic acid.

The above-mentioned inventive method is usable in an experiment of detecting an arbitrary particle using various light-emitting probes. For example, the inventive method is applicable to an experiment, in which a substance having an energy donor site and an energy acceptor site between which a fluorescence energy transfer phenomenon occurs and capable of being decomposed by a predetermined decomposition reaction when the substance has bound to a certain particle is employed as a light-emitting probe; this light-emitting probe is added in a sample solution to be tested; the light from the sample solution is detected; and whether or not the light-emitting probe having bound to the above-mentioned particle, namely whether or not the above-mentioned particle exists in the sample solution is checked in accordance with the presence or absence of a fluorescence energy transfer phenomenon. That is, according to one manner of the above-mentioned invention, there is provided a method characterized in that a light-emitting probe has an energy donor site and an energy acceptor site producing a fluorescence energy transfer; the step of preparing a sample solution comprises a step of conducting a reaction to decompose the light-emitting probe having bound to the particle to be detected and the light to be detected is light emitted from the light-emitting probe decomposed by the above-mentioned reaction.

Effect of Invention

The optical analysis technique realized by the above-mentioned inventive method employs, for its light detecting mechanism itself, a structure to detect light from a light detection region in a confocal microscope or a multiphoton microscope similarly to the cases of optical analysis techniques, such as FCS, FIDA and PCH, and thus the amount of a sample solution may be similarly small. However, since no statistical procedure of computing the fluorescence intensity fluctuation is performed in the present invention, the inventive optical analysis technique is applicable to a sample solution in which the number density or concentration of a particle is substantially lower than the level required for the optical analysis techniques, such as FCS, FIDA and PCH.

Moreover, since each particle dispersed or dissolved in a solution is individually detected in this invention, it becomes quantitatively possible by using the information thereof to conduct the counting of particles, the computation of the concentration or number density of a particle in a sample solution or the acquisition of the information on the concentration or number density. For example, although patent documents 5 and 6 could acquire the correlation between the aggregate in the frequency of fluorescence signals having an intensity beyond a predetermined threshold value within a predetermined time and the number of particles of fluorescent molecules, etc. in a sample solution, it is impossible to grasp the dynamic behavior of a particle passing through the measuring region (whether a particle passes straight through the measuring region or dwells within the measuring region), and therefore the correspondence between a fluorescence signal having an intensity higher than a predetermined threshold value and a particle passing through the measuring region is not clear, so that the counting of light-emitting particles was theoretically impossible and it was difficult to determine precisely the concentration of particles in a sample solution. However, since, according to this invention, a particle passing through a light detection region is made associated with a detected light signal in 1 to 1 manner so that one particle will be detected at one time, the counting of particles dispersed and moving at random in a solution becomes possible, and it becomes possible to determine the concentration or number density of the particle in a sample solution precisely as compared with the conventional art. Actually, as described in the column of embodiments, it has been found that, according to the inventive method of detecting individually particles in a sample solution using a light-emitting probe; counting those number and determining the particle concentration, it is possible to determine a concentration much lower than the concentration which can be determined based upon the fluorescence intensity measured by a fluoresce spectrometer or a plate reader. In addition, with respect to a system in which two or more light-emitting probes bind to one particle, it has been found that the particle concentration in a solution can be determined more accurately not only in the lower concentration side but also in the higher concentration side, in comparison with the prior art.

Furthermore, according to the manner of scanning the inside of a sample solution with a light detection region by changing the optical path of an optical system, since the inside of a sample solution will be observed under a uniform condition where a sample solution is mechanically stabilized without mechanical vibration and a hydrodynamic action to the sample solution, the reliability of a quantitatively detected result is improved as compared with e.g., the case in which a flow is made generated in a sample (When a flow is given, it is difficult to give an always uniform flow speed and the device structure becomes complicated, and also, the required sample amount increases substantially, and the particles, light-emitting probes, their combinations or other substances in the solution may deteriorate or be denaturalized by the hydrodynamic action owing to the flow), and it becomes possible to perform a measurement under a condition without influences or artifacts due to dynamic action against a particle to be a detected object in a sample solution.

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device according to the present invention. FIG. 1B is a schematic diagram of a confocal volume (an observation region of a confocal microscope). FIG. 1C is a schematic diagram of the mechanism for changing the direction of the mirror 7 to move the position of a light detection region in a sample solution.

FIGS. 3A-3H are drawings showing schematically examples of structures for preventing the detection of light of a light-emitting probe having not bound to a particle.

Figure 5A:
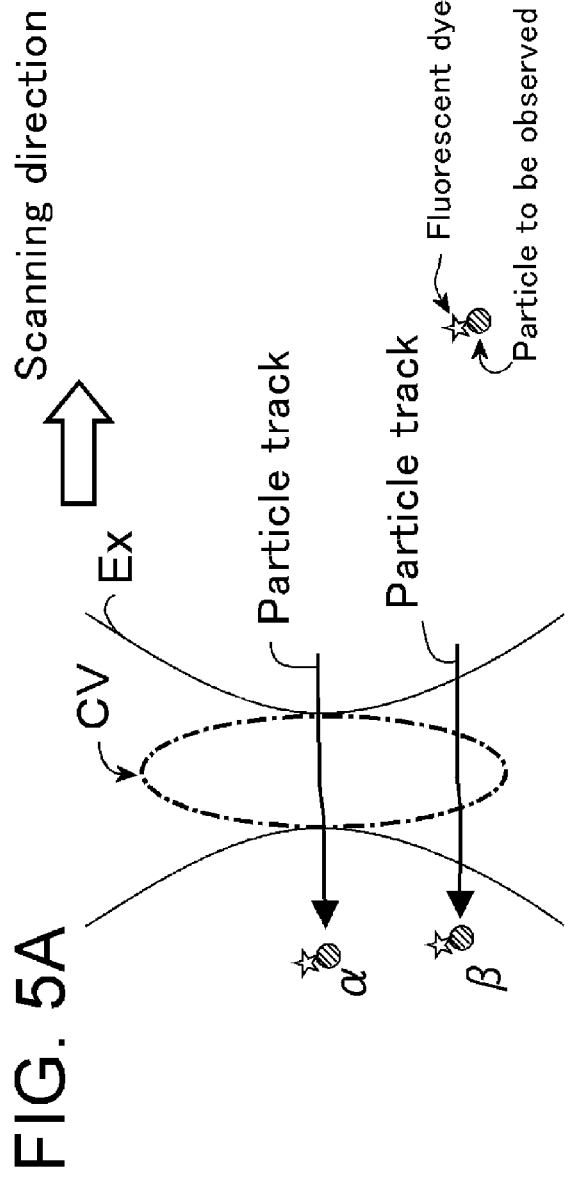
Figure 5B:
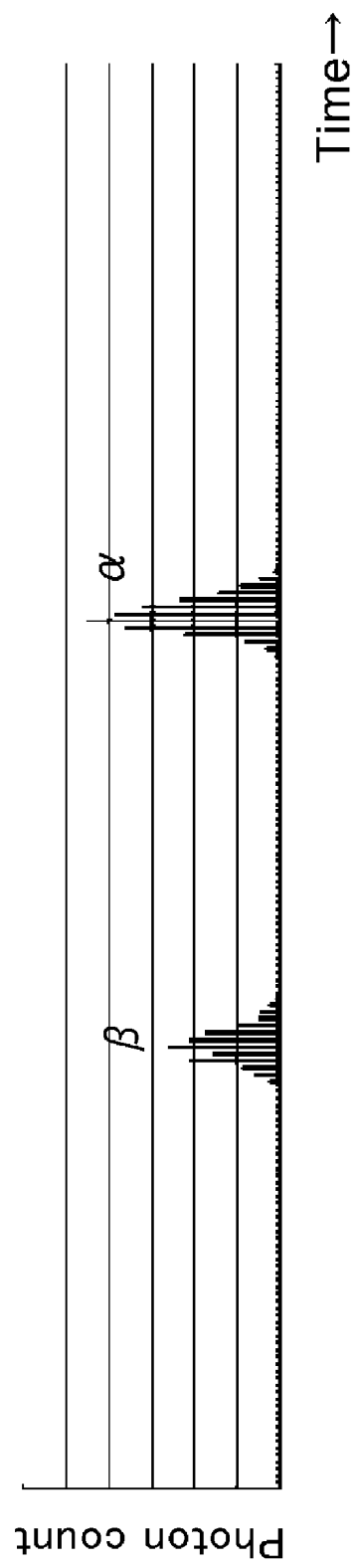

FIGS. 5A and 5B are a drawing of a model in the case that a particle to be observed crosses a light detection region by moving the position of the light detection region in a sample solution at a velocity quicker than the diffusional moving velocity of the particle to be observed, and a diagram showing the example of the variation of the photon counts (light intensity) with time in this case, respectively.

Figure 6:
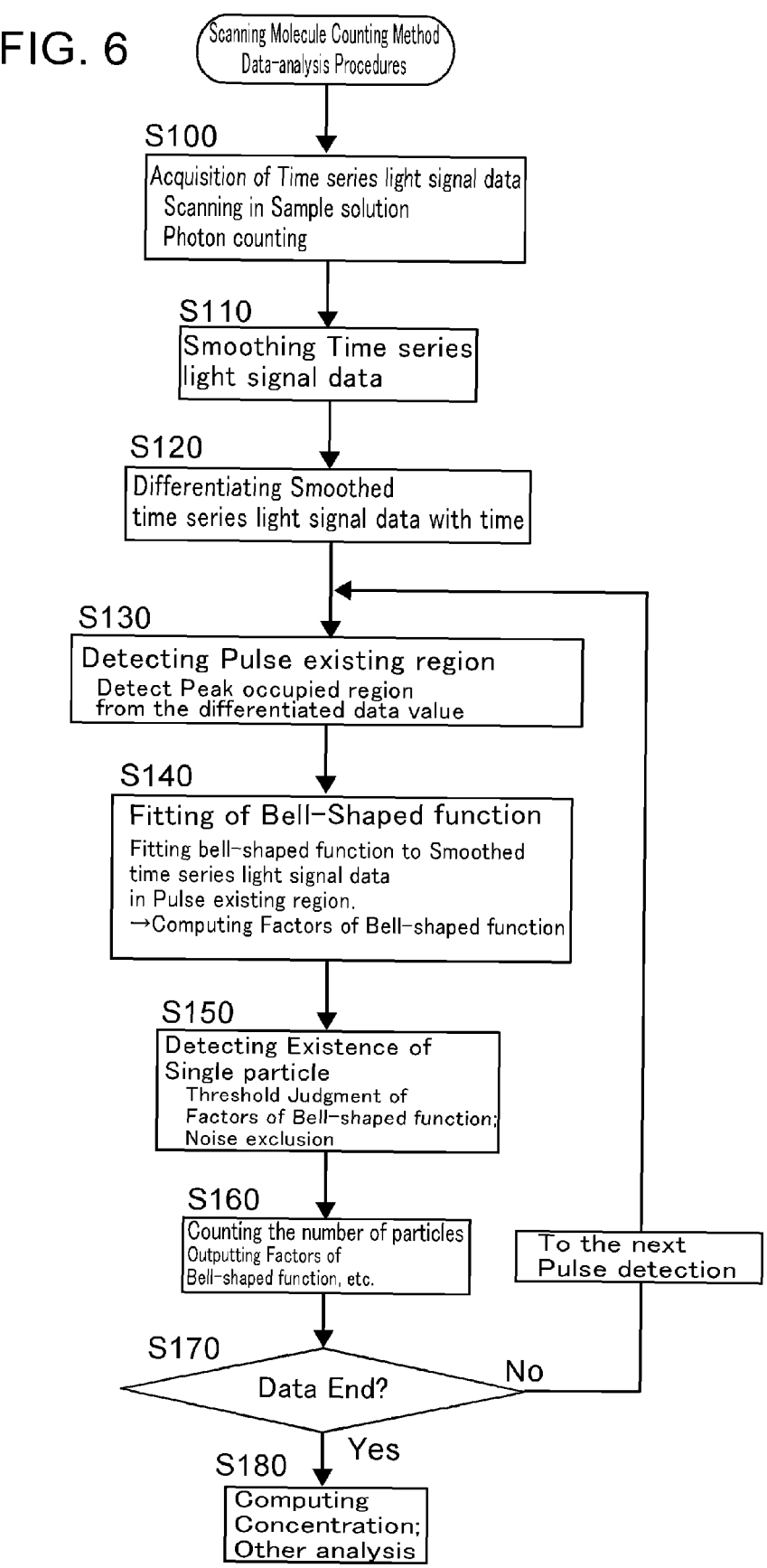

FIG. 6 is a drawing showing the procedures in the form of a flow chart for the counting of particles from the time variation of photon counts (light intensity) measured by the inventive method.

Figure 7A:
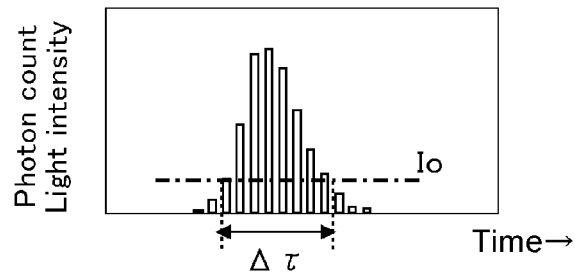
Figure 7B:
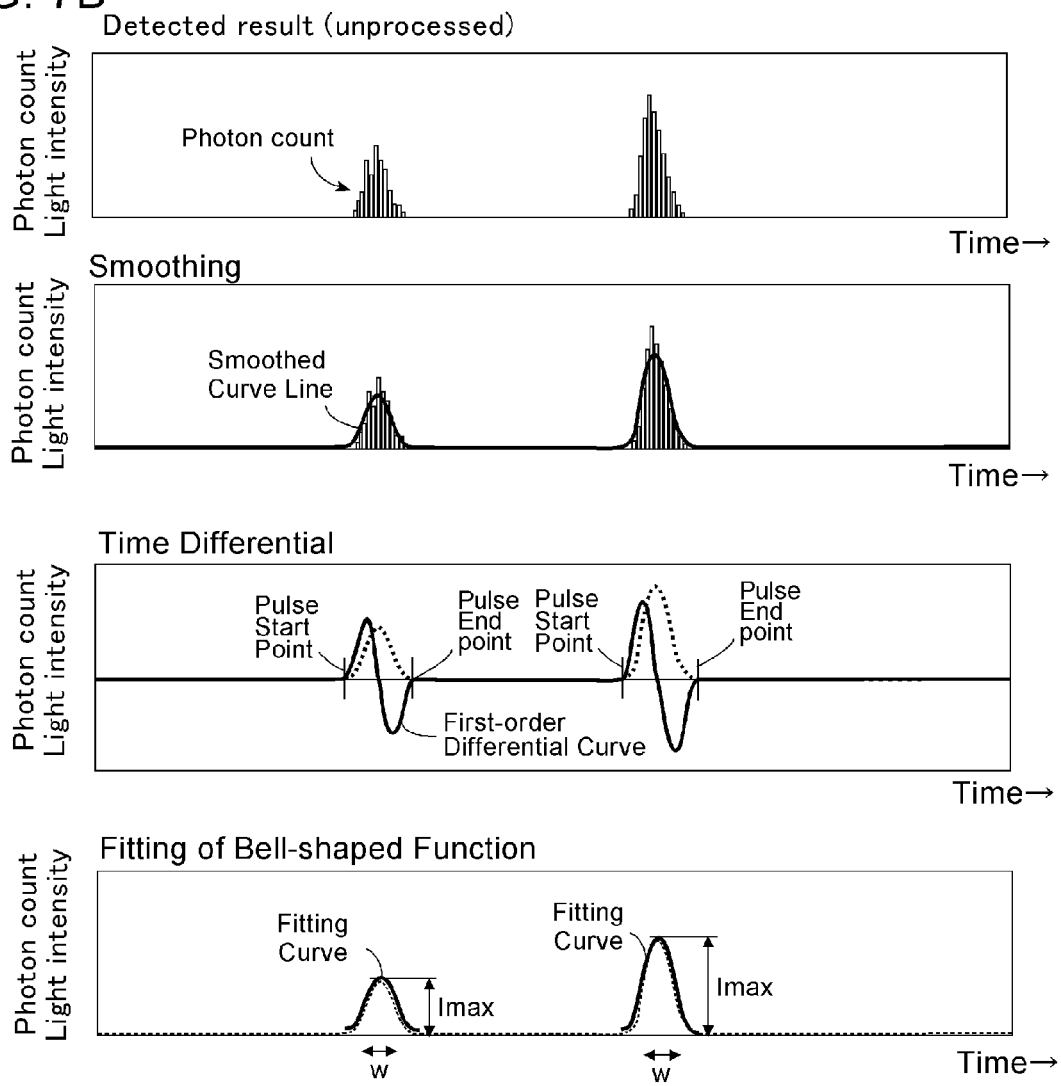

FIGS. 7A and 7B are drawings explaining one example of a signal processing step of the detected signals in the procedure for conducting the counting of particles from the time variation of the photon counts (light intensity) measured by the inventive method.

Figure 8:
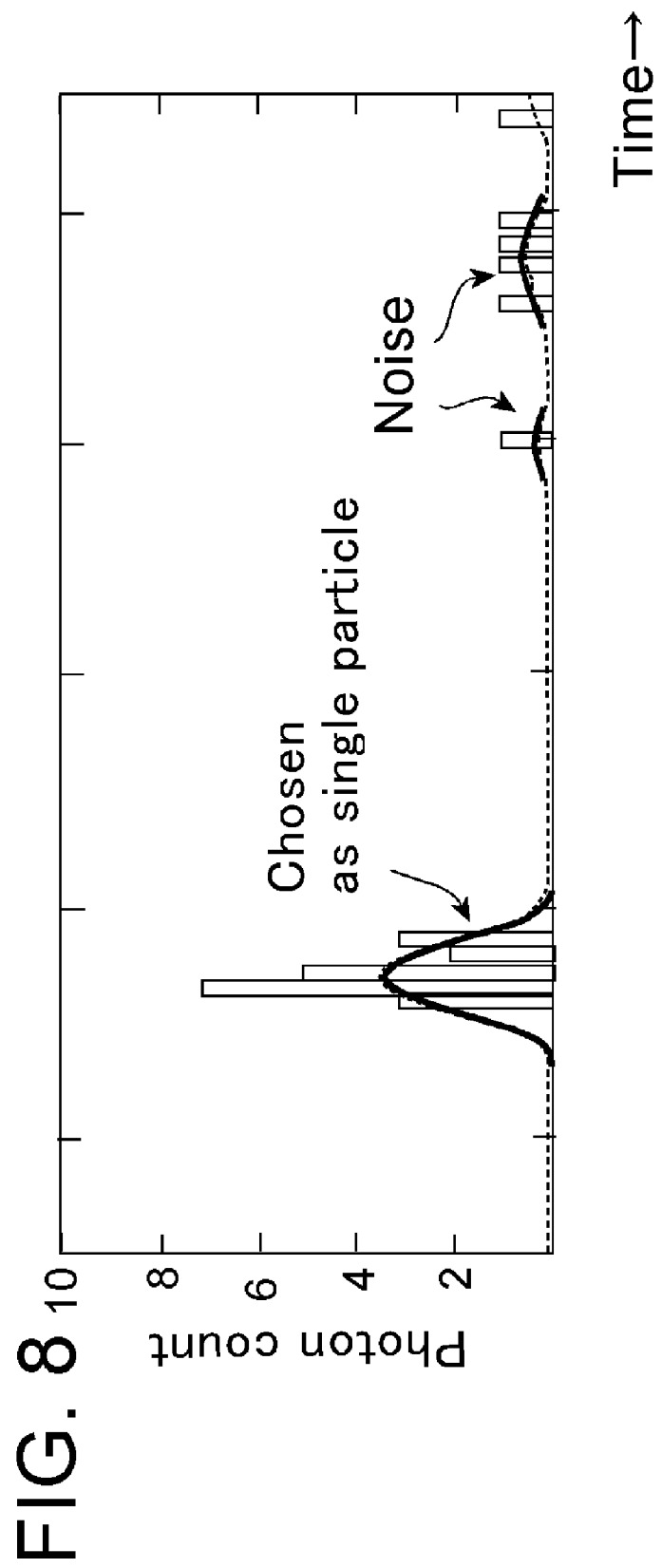

FIG. 8 shows examples of photon count data measured by the inventive method (bar graph); curve obtained by carrying out the smoothing of the data (dotted line); and gauss functions fitted on the pulse existing regions (solid line). In the drawing, the signals attached with "noise" are disregarded as signals due to noises or contaminants.

FIGS. 9A, 9B and 9C each show results of nucleic acid concentration detection experiments in accordance with the inventive method, results of nucleic acid concentration detection experiments using a plate reader and schematic diagrams of the condition of molecules in the nucleic acid concentration detection experiments.

Figure 10B:
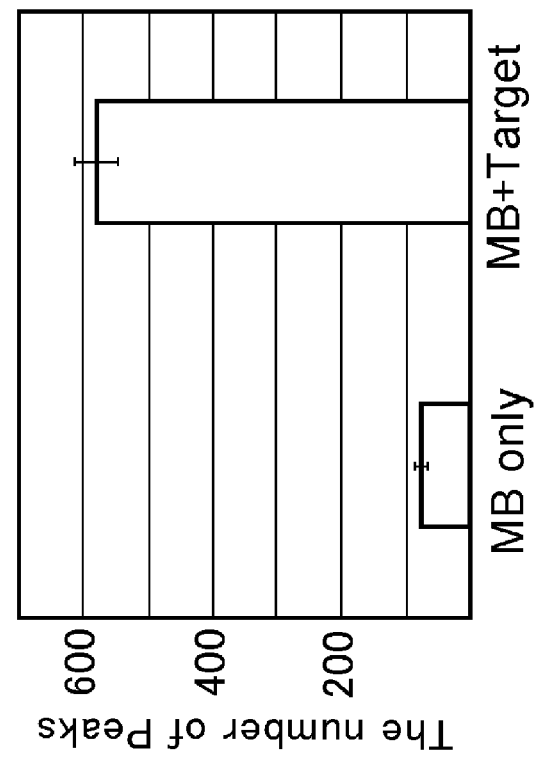
Figure 10A:
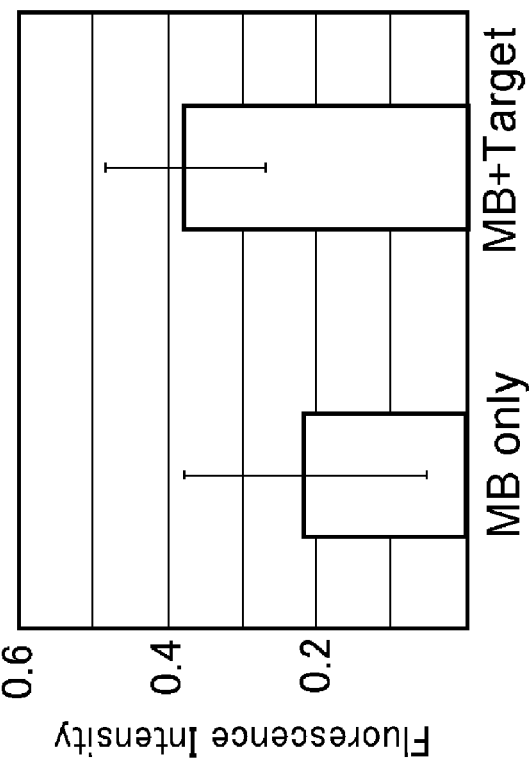

FIGS. 10A and 10B each show experimental results of detecting a nucleic acid having a certain base sequence using a molecular beacon in accordance with the inventive method, and experimental results of detecting a nucleic acid having a certain base sequence using a molecular beacon with a plate reader.

Figure 11:
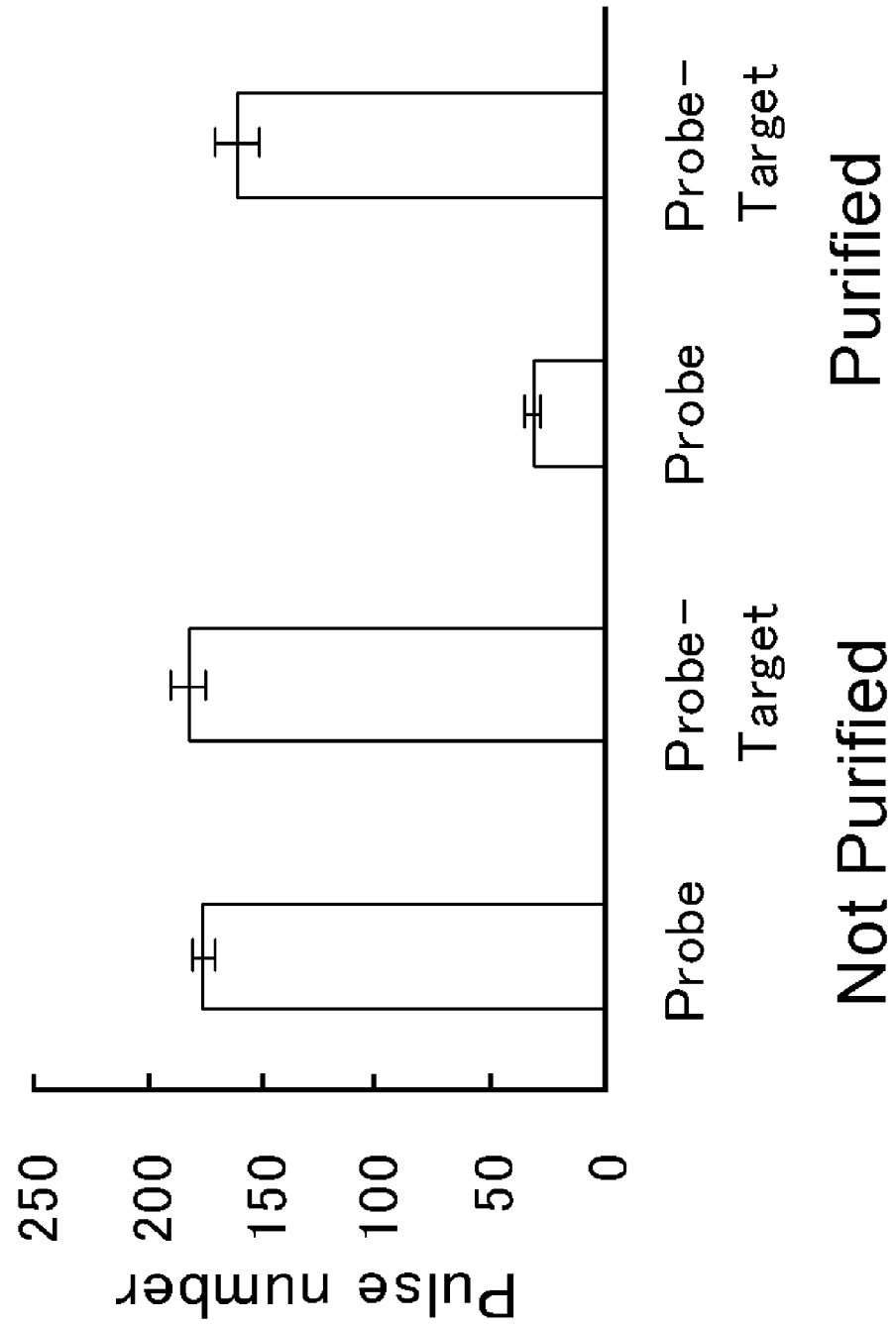

FIG. 11 shows results of experiments of detecting a particle to be observed in a sample solution from which unreacted fluorescence-labeled probes have been removed by a physical purification in accordance with the inventive method. In the drawing, a bar graph is an average, and an error bar is a standard deviation.

Figure 12A:
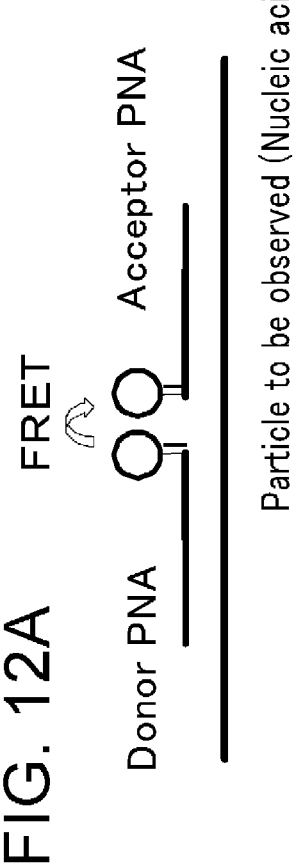
Figure 12B:
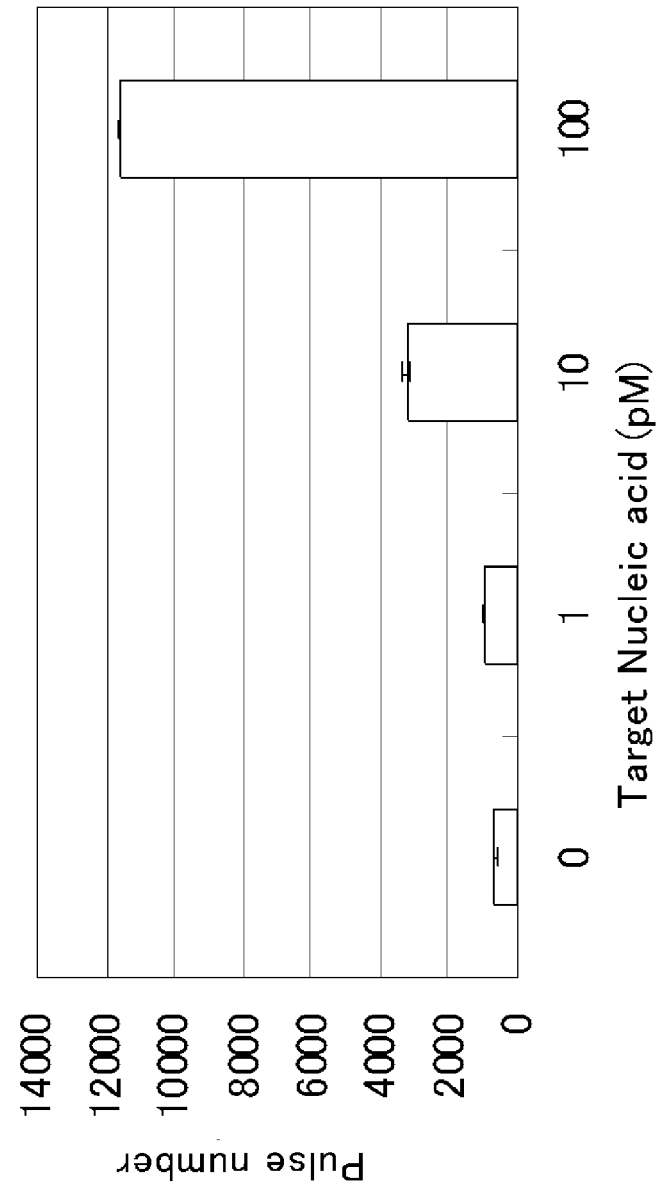

FIG. 12A is a drawing showing schematically the conditions of molecules in experiments of detecting a nucleic acid using a fluorescence energy transfer (FRET) in accordance with the inventive method, and FIG. 12B shows results of the detected pulse numbers in the experiments. In the drawing, a bar graph is an average, and an error bar is a standard deviation.

FIG. 13A is a drawing showing schematically the conditions of molecules in experiments of detecting a nucleic acid (a particle to be observed) using the fluorescence quenching method in accordance with the inventive method, and FIG. 13B shows results of the detected pulse numbers in the experiments. In the drawing, a bar graph is an average, and an error bar is a standard deviation.

Figure 14A:
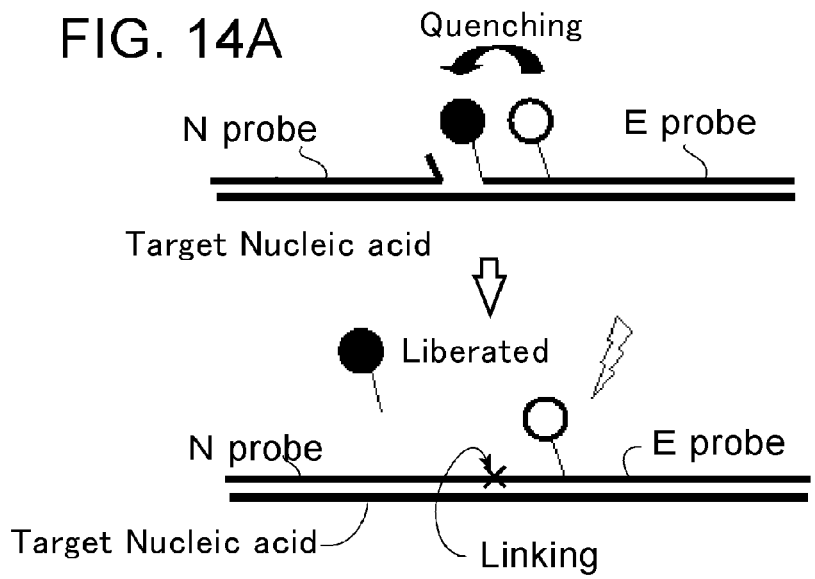
Figure 14B:
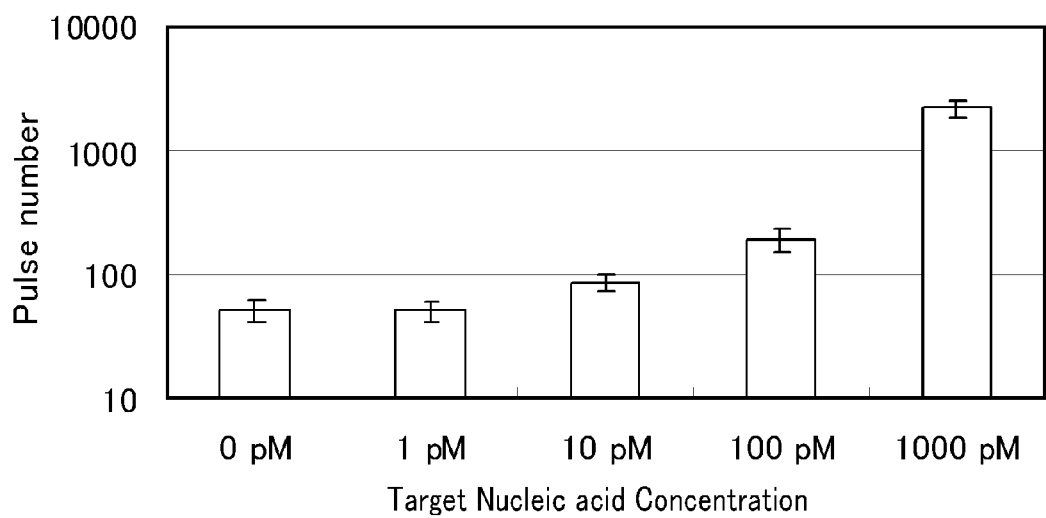

FIG. 14A is a drawing showing schematically the conditions of molecules in experiments of detecting a nucleic acid using a QUAL reaction in accordance with inventive method, and FIG. 14B shows results of the detected pulse numbers in the experiments. In the drawing, a bar graph is an average and an error bar is a standard deviation.

FIG. 15 shows examples of the time variation of the photon count (light intensity) obtained in a conventional optical analysis technique computing fluorescence intensity fluctuation, where FIG. 15A shows a case that the particle concentration is at a level providing a sufficient precision in the measurement, and FIG. 15 B shows a case that the particle concentration in a sample is significantly lower than the case of (A).

EXPLANATIONS OF REFERENCE NUMERALS

1 - - - Optical analysis device (confocal microscope)
2 - - - Light source
3 - - - Single mode optical fiber
4 - - - Collimating lens
5, 14a - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14 - - - Barrier filter
15 - - - Multi-mode optical fiber
16 - - - Photodetector
17 - - - Mirror deflector
17a - - - Stage position changing apparatus
18 - - - Computer

DESCRIPTION OF EMBODIMENTS

Figures 1A, 1B, 1C:
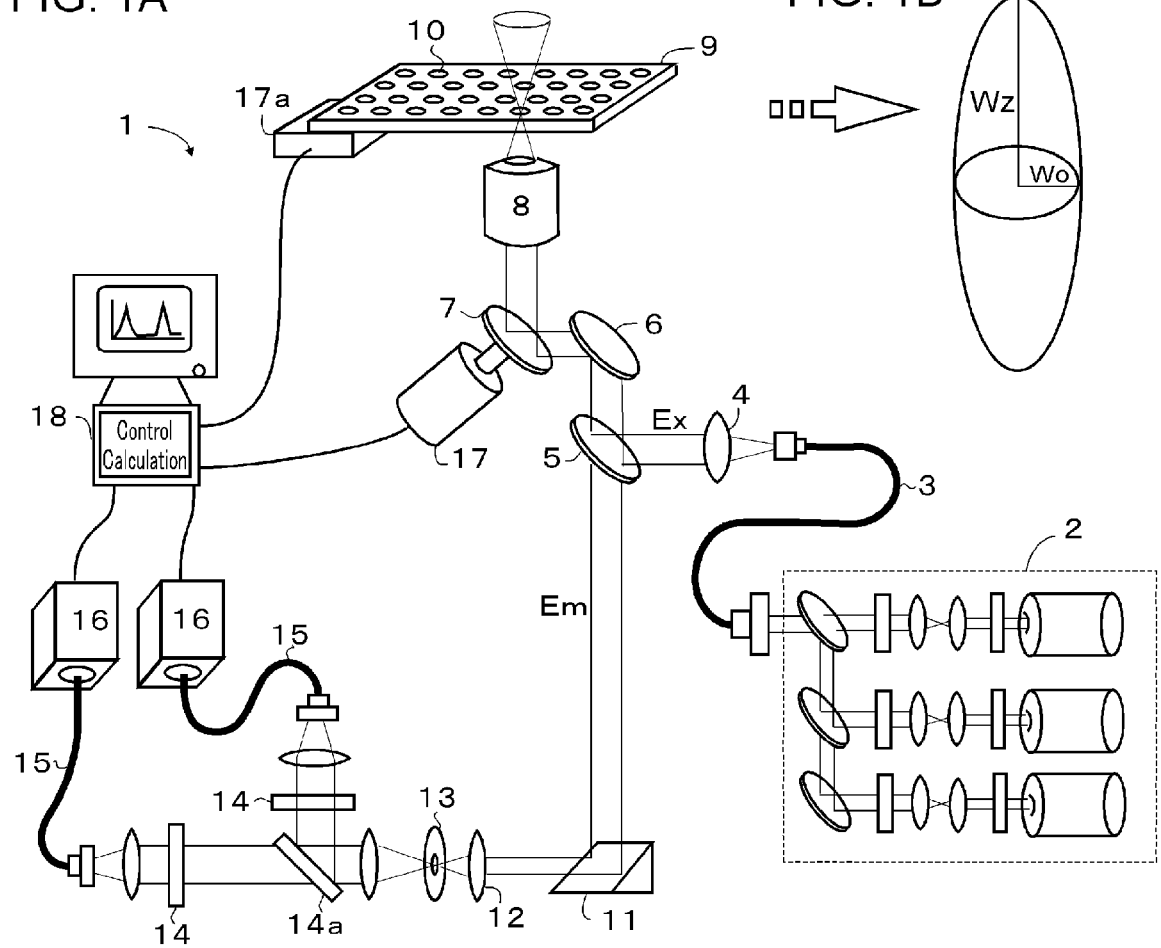

In the followings, preferable embodiments of the present invention are described in detail.
The Structure of an Optical Analysis Device
In the basic structure, the inventive method can be realized with an optical analysis device formed by combining an optical system of a confocal microscope and a photodetector as schematically illustrated in FIG. 1A, with which FCS, FIDA, etc. can be performed. Referring to the drawing, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light emitted from a light source 2 and transmitted through the inside of a single mode fiber 3 (Ex) forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, particles to be observed objects and light-emitting probes binding to the particles, which probes are molecules to which a light emitting label such as a fluorescent dye is attached, are dispersed or dissolved, and when a particle which has bound to or associated with a light-emitting probe (a light-emitting probe dissociated from a particle after once binding to the particle, depending on an experimental manner) enters into the excitation region, the light-emitting probe is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13; transmits through a barrier filter 14 (where light components only in a specific wavelength band region are selected); and is introduced into a multimode fiber 15, reaching to a photodetector 16, and after the conversion into time series electric signals, the signals are inputted into the computer 18, where the processes for optical analyses are executed in manners explained later. In this regard, as known in ones skilled in the art, in the above-mentioned structure, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region in this optical analysis device, whose effective volume is usually about 1-10 fL (Typically, the light intensity is spread in accordance with a Gaussian type or Lorentz type distribution having the peak at the center of the region. The effective volume is a volume of an approximate ellipsoid bordering a surface where the light intensity reduced to $1/e^2$ of the peak intensity), which is called as "confocal volume". Moreover, since the light from one particle and light-emitting probe combination or one light-emitting probe, for example, the faint light from one or several fluorescent dye molecule(s), is detected in this invention, preferably, a super high sensitive photodetector, usable for the photon counting, is used for the photodetector 16. Further, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18. According to this structure, quick measurement can be achieved even in the presences of two or more specimens.

Furthermore, in the optical system of the above-mentioned optical analysis device, there is provided a mechanism for changing the optical path of the optical system to scan the inside of the sample solution with the light detection region, namely to move the position of the focal region i.e., the light detection region, within the sample solution. For this mechanism for moving the position of the light detection region, for example, as schematically illustrated in FIG. 1C, there may be employed a mirror deflector 17 which changes the direction of the reflective mirror 7. This mirror deflector 17 may be the same as that of a galvanomirror device equipped on a usual laser scan type microscope. Also, in order to attain a desired moving pattern of the position of the light detection region, the mirror deflector 17 is driven in harmony with the light detection of the photodetector 16 under the control of the computer 18. The movement track of the position of the light detection region may be arbitrarily selected from circular, elliptical, rectangular, straight and curvilinear ones, or a combination of these (The program in the computer 18 may be designed so that various moving patterns can be selected). In this regard, although not illustrated, the position of the light detection region may be moved in the vertical direction by moving the objective 8 up and down. As noted, according to the structure of changing the optical path of the optical system to move the position of the light detection region instead of moving the sample solution, neither mechanical vibration nor hydrodynamic action occur substantially in the sample solution, and consequently it becomes possible to eliminate the influence of a dynamic action on an object to be observed, achieving the stable measurement.

In the case that a particle and light-emitting probe combination or a light-emitting probe emits light by multiple photon absorption, the above-mentioned optical system is used as a multiphoton microscope. In that case, since the light is emitted only from the focal region of the excitation light (light detection region), the pinhole 13 may be removed. Further, in the case that a particle and light-emitting probe combination or a light-emitting probe emits light owing to a chemiluminescence or bioluminescence phenomenon without excitation light, the optical system 2-5 for generating excitation light may be omitted. When a particle and light-emitting probe combination or a light-emitting probe emits light owing to phosphorescence or scattered light, the above-mentioned optical system of the confocal microscope is used as it is. Furthermore, in the optical analysis device 1, as shown in the drawing, two or more excitation light sources 2 may be provided so that the wavelength of the excitation light can be selected appropriately in accordance with the excitation wavelength of a particle and light-emitting probe combination or a light-emitting probe. Similarly, two or more photodetectors 16 may also be provided so that, when the sample contains two or more kinds of particle and light-emitting probe combinations or light-emitting probes whose wavelengths differ from one another, the respective lights from them can be detected separately in accordance with the wavelengths.

The Principle of the Inventive Optical Analysis Technique

Spectral analysis techniques, such as FCS and FIDA, are advantageous in that the required sample amount is extremely small and a test can be performed promptly as compared with the conventional biochemical analytical techniques. However, in these spectral analysis techniques such as FCS and FIDA, the concentration and characteristics of a particle to be observed are principally computed based on the fluorescence intensity fluctuation, and therefore, in order to obtain accurate measurement results, the concentration or number density of the particle to be observed in a sample solution should be at a level where about one particle to be observed always exists in a light detection region CV during the fluorescence intensity measurement as schematically drawn in FIG. 15A so that significant light intensity (photon count) can be always detected in the measuring term as shown in the right-hand side of the drawing. When the concentration or number density of the particle to be observed is lower than that, for example, at the level where the particle to be observed rarely enters into the light detection region CV as drawn on FIG. 15B, no significant light intensity (photon count) would appear in a part of the measuring term as illustrated on the right-hand side of the drawing, and thus, accurate computation of light intensity fluctuation would become difficult. Also, when the concentration of the particle to be observed is significantly lower than the level where about one particle to be observed always exists in the inside of the light detection region during the measurement, the calculation of light intensity fluctuation would become subject to the influence of the background, and the measuring term should be made long in order to obtain the significant quantity of the light intensity data (photon count), sufficient for the calculation.

Then, in the present invention, there is proposed an optical analysis technique based on a new principle which enables the detection of characteristics of a particle to be observed, such as its number density or concentration, even when the concentration of the particle to be observed is lower than the level requested in the above-mentioned spectral analysis techniques, such as FCS and FIDA.

Figure 2A:
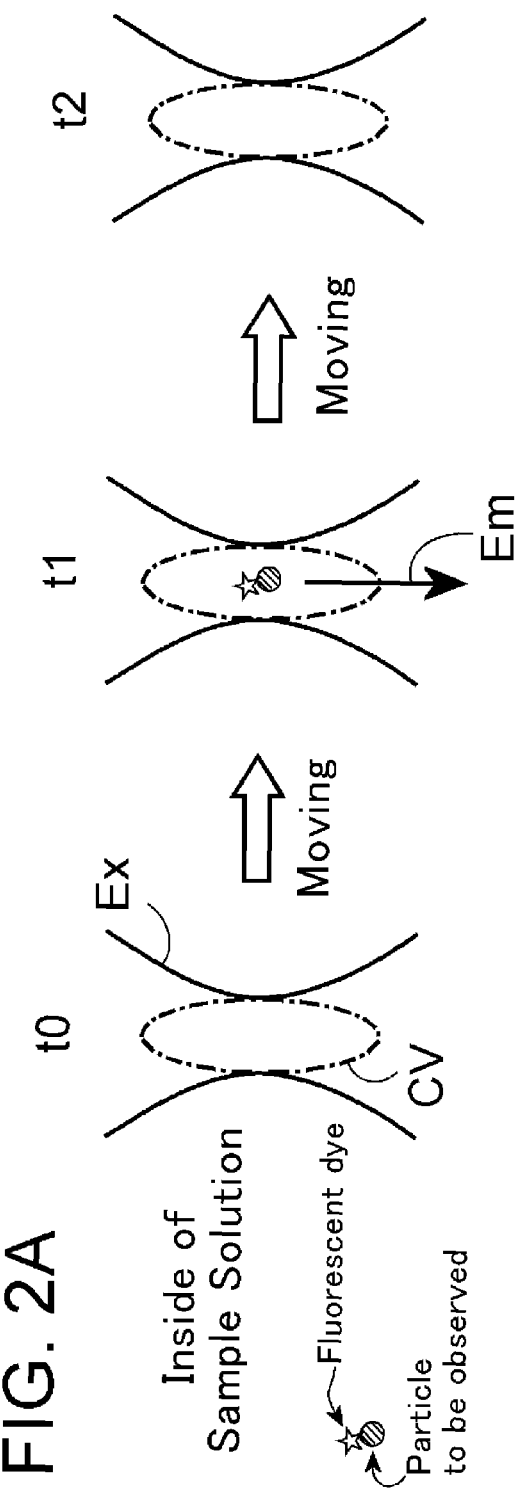
FIGS. 2A and 2B are a schematic diagram explaining the principle of the light detection by the optical analysis technique according to the present invention and a schematic diagram of the variation of the measured light intensity with time, respectively.
Figure 2B:
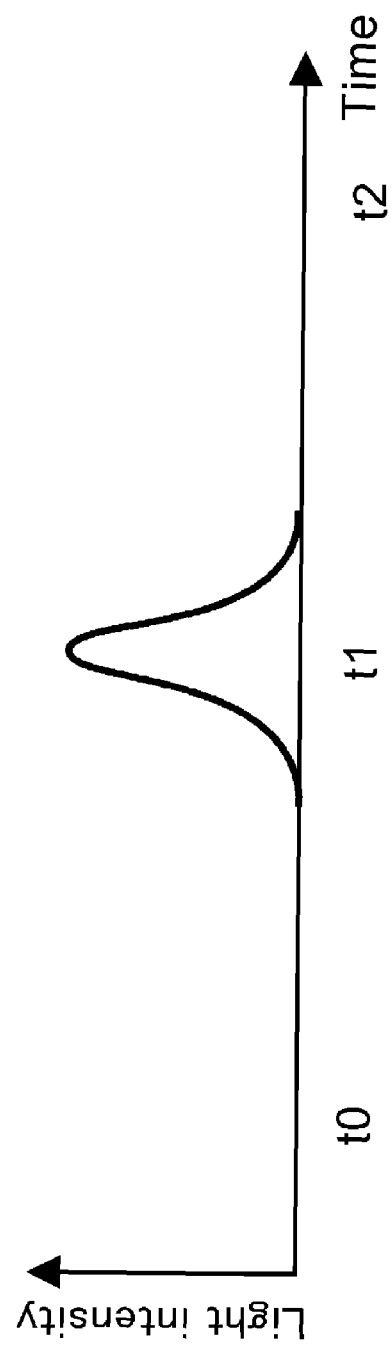

In the inventive optical analysis technique, briefly speaking, as the processes to be performed, the light detection is performed together with moving the position of the light detection region CV in a sample solution, namely, scanning the inside of the sample solution with the light detection region CV by driving the mechanism (mirror deflector 17) for moving the position of the light detection region to change the optical path as schematically drawn in FIG. 2. Then, for example, as in FIG. 2A, during the moving of the light detection region CV (in the drawing, time to-t2), when the light detection region CV passes through a region where one particle (In the drawing, a fluorescent dye is attached as a light-emitting probe) exists (t1), a significant pulsed light intensity (Em) will be detected as drawn in FIG. 2B. Thus, by detecting, one by one, each significant light intensity appearing as illustrated in FIG. 2B during the execution of the moving of the position of the light detection region CV and the light detection as described above, the particle bound to the light-emitting probe are detected individually, and by counting the number thereof, the information about the number, concentration or number density of the particles existing in the measured region can be acquired. It should be understood that, in the principle of this inventive optical analysis technique, no statistical calculation processes, such as the calculation of the fluorescence intensity fluctuation, are conducted and the particles are one by one detected, and therefore, the information about the concentration or number density of the particle is acquirable even in a sample solution with a low particle concentration at the level where no sufficiently precise analysis is available in FCS and FIDA.

Moreover, as shown in the embodiments described later, by the method of detecting individually particles in a sample solution and counting them in accordance with the present invention, it becomes possible to measure a lower concentration of fluorescently labeled particle than that measurable from the fluorescence intensity measured with a fluorescence spectrophotometer and a plate reader. In the measurement of a concentration of a certain fluorescently labeled particle with a fluorescence spectrophotometer or a plate reader, usually, it is assumed that the fluorescence intensity is proportional to the concentration of a fluorescently labeled particle. However, in that case, when the concentration of a fluorescently labeled particle is significantly low, the amount of noise signals becomes large relative to the amount of signals of the light emitted from the fluorescently labeled particles (Deterioration of the S/N ratio), and thereby, the proportionality relation between the concentration and the amount of light signals of the fluorescently labeled particles collapses and the accuracy of the determined concentration value deteriorates. On the other hand, in the inventive method, noise signals are eliminated from the detected result in the step of detecting the signals corresponding to the respective particles from the detected light signals, and the concentration is computed by counting only the signals corresponding to the respective particles, and therefore, it becomes possible to detect a lower concentration than in a case that a concentration of a particle is detected under the assumption that fluorescence intensity is proportional to a concentration of a fluorescently labeled particle.

Furthermore, in a case that a plurality of light-emitting probes bind to one particle to be observed, by the method of detecting individually particles in a sample solution and counting them in accordance with the present invention, the accuracy of measurement of the particle concentration on the side of higher particle concentration is also improved in comparison with the conventional method in which the concentration is determined under the assumption that fluorescence intensity is proportional to a concentration of a fluorescently labeled particle. When a certain amount of light-emitting probes is added in a sample solution in a case that a plurality of light-emitting probes bind to one particle to be observed, as the concentration of a particle to be observed becomes higher, the number of the light-emitting probes binding to a particle relatively decreases. In that case, since the fluorescence intensity per particle to be observed may decrease, the proportionality between the concentration and the amount of light of the fluorescently labeled particles collapses, and thereby the accuracy of the determined concentration value deteriorates. On the other hand, in the inventive method, the influence due to the reduction of the fluorescence intensity per particle is small in the step of detecting the signals corresponding to the respective particles from the detected light signals, and the concentration is computed from the particle count, and thereby, it becomes possible to detect a concentration to the level higher than in the case of detecting a concentration under the assumption that fluorescence intensity is proportional to a concentration of a fluorescently labeled particle.

Operation Processes in the Invention

In the inventive method with the inventive optical analysis device 1 as illustrated in FIG. 1A, concretely, there are conducted (1) preparation of a sample solution containing light-emitting probes and particles to be observed to which the probes bind, (2) a process of measuring the light intensity of a sample solution and (3) a process of analyzing the measured light intensity.

(1) Preparation of a Sample Solution

The particle to be observed in the inventive method may be an arbitrary particle as long as it is dispersed and moving at random in a sample solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecule. The particles to be observed are typically mixed with light-emitting probes, provided with a light emitting label (a fluorescent molecule, a phosphorescent molecule, a chemiluminescent or bioluminescent molecule) in an arbitrary manner, in a sample solution (Typically, it is an aqueous solution, but not limited to this, and it may be an organic solvent or other arbitrary liquids), in which a light-emitting probe binds to or associates with a particle to be observed to form a combination so that the light emitted by the light-emitting probe will serve as the mark of the existence of the particle to be observed, thereby enabling the detection of the particle to be observed (As stated later, in some experimental ways, a particle to be observed is detected by detecting a light-emitting probe which had bound to the particle to be observed once and then has been dissociated from the particle to be observed through a predetermined treatment). As an example of a particle-to-be-observed and light-emitting probe combination, when a particle to be observed is a nucleic acid, there will be employed for a light-emitting probe a nucleic acid or a nucleic acid analogue having the base sequence complementary to the nucleic acid to be the particle to be observed, a nucleic-acid binding protein, a nucleic-acid binding antibody, etc. As a concrete example, there may be raised a case that a fluorescently labeled antibody discriminating a DNA-RNA hybrid is used as a light-emitting probe when the particle to be observed is an association of DNA-RNA (hybrid capture method).

As noted above, with respect to the mixing of a particle to be observed and a light-emitting probe to form a particle and light-emitting probe combination, it should be minded that substantially all the particles to be observed are required to have bound to or associated with a light-emitting probe in a sample solution. Namely, if there are particles to be observed, having not bound to or associated with a light-emitting probe, the number and/or concentration of particles to be observed in the sample solution would be estimated to be lower by their number. Thus, in order to certainly make substantially all the particles to be observed bind to or associate with a light-emitting probe, it is required in the formation of the particle and light-emitting probe combination to add into the sample solution the light-emitting probes such that the number of the light-emitting probes exceeds beyond the number of the particles to be observed in the sample solution. However, in that case, of course, as the result, the light-emitting probes neither binding to nor associating with a particle to be observed become present in the sample solution, and, if the light from a light-emitting probe having not bound to the particle to be observed or a single light-emitting probe is detected without being distinguished from the light from the particle and light-emitting probe combination, the accuracy in the detection of the particle to be observed would deteriorate, also. Thus, in the inventive method by the optical analysis technique which detects a particle to be observed individually using a light-emitting probe, preferably, there may be employed a structure for preventing the detection of the light of a light-emitting probe having not bound to a particle to be observed or a single light-emitting probe, namely, a structure which eliminates from the detected result the light from a light-emitting probe having not bound to a particle to be observed or a single light-emitting probe. As such a structure, for example, the following structures may be employed.

(i) Separation of a Light-Emitting Probe Having not Bound to a Particle to be Observed Out of a Sample Solution In one of the structures for eliminating from the detected result the light from a light-emitting probe having not bound to a particle to be observed, as schematically shown in FIG. 3A, after formation of a particle and light-emitting probe combination, a light-emitting probe having not bound to a particle to be observed or a single light-emitting probe may be separated and removed from a sample solution by an arbitrary method of separating two or more substances physically through utilizing the difference in characteristics, such as the difference in size or molecular weight, an affinity to an arbitrary substance, electrically charged condition, etc., between the light-emitting probe having not bound to the particle to be observed or the single light-emitting probe and the particle and light-emitting probe combination or the light-emitting probe having bound to the particle to be observed. Concretely, there may be employed a physical separation technique of substances usually performed in this field, such as operations including adsorption, extraction or washing through chromatography (hydrophilic/hydrophobic chromatography, affinity chromatography, ion exchange chromatography etc.), ultra-filtration, electrophoresis, phase separation, centrifugal separation, solvent extraction, filter adsorption, etc. Moreover, there may be used a method of eliminating single light-emitting probes from a sample solution, as ELISA method, in which, into a sample solution where particles to be observed and light-emitting probes have been mixed, different probes binding to particles to be observed (probe for separation) are further mixed to bind to the particles to be observed; and then the sample solution is exposed to a carrier which binds to the probes for separation so that only the combination consisting of the particle to be observed, light-emitting probe and the probe for separation will be held, while the single light-emitting probes are separated and removed from a sample solution (for example, by washing).

(ii) Use of a Fluorescent Dye Whose Wavelength Characteristic Changes

In this field, there are known various fluorescent dyes whose wavelength characteristic changes, depending upon whether or not it has bound to a certain substance. Then, in order to eliminate the light of a light-emitting probe having not bound to a particle to be observed or a single light-emitting probe from the detected result, there may be employed, for a light-emitting probe, a fluorescent dye whose wavelength characteristic changes when it binds to a particle to be observed, as schematically drawn on FIG. 3C. When such a light-emitting probe is employed, it becomes possible to selectively detect the light from a particle-to-be-observed and light-emitting probe combination or a light-emitting probe having bound to a particle to be observed by selectively detecting the light emitted from the light-emitting probe when it has bound to a particle to be observed without requiring operations for eliminating physically single light-emitting probes or light-emitting probes having not bound to a particle to be observed. Such a fluorescent dye may be a dye whose excitation and/or emission wavelength changes when it binds to a particle to be observed or a dye whose fluorescence intensity notably increases when it binds to a particle to be observed. Exemplarily, when a particle to be observed is a nucleic acid or a nucleic acid analogue, intercalator fluorescent dyes of nucleic acid (Ethidium bromide, Acridine orange, SYTOX Orange, SYTOX Red, SYBR Green I, SYBR Green II, SYBR Gold, Picogreen, OllGreen, Gel Red, Gel Green, Ribo Green, EvaGreen and a dye having a cyanine skeleton, etc.) are employable. Further, when a particle to be observed is a protein, a dye whose fluorescence intensity and fluorescence wavelength change owing to peripheral environmental change when it binds with a protein, is employable as a light-emitting probe. For such a dye, the following fluorescent dyes are useable: e.g. Naphthalene sulfonic acids, which is a hydrophobic probe, such as 1-anilinonaphthalene-8-sulfonic acid (ANS), N-methyl-2-anilinonaphthalene-6-sulfonic acid (MANS), 2-p-toluidinylnaphthalene-6-sulfonic acid (TNS), Dimethylamino naphthalenes (dansyl), dyes liable to be affected by the influence of local pH or dielectric constant, such as TAMRA, Fluorescein, 6-joe, BODIPY, TMR, BODIPY TR, Alexa 488, Alexa 532, BODIPY FL, BODIPY FL/C3, BODIPY FL/C6, FITC, EDANS, Rhodamine 6G, TMR, TMRITC, x-rhodamine, Texas Red, BODIPY 5-FAM, BODIPY R6G, BODIPY 581.

Moreover, in addition to fluorescent dyes as described above, a substance consisting of at least two components, which emits fluorescence when the mutual position of the at least two components changes when the substance binds to a particle to be observed, can be employed as a light-emitting probe whose wavelength characteristic changes if it binds to a particle to be observed. As examples of such a substance, there can be raised a fluorescent protein which structurally changes to emit strong fluorescence when it binds to a certain particle or a molecule which assembles to form a fluorescent metal complex when it binds with a certain particle (Ligand of a complex).

(iii) Use of a Fluorescence Energy Transfer Phenomenon

As an alternative structure for eliminating the light of a light-emitting probe having not bound to a particle to be observed from the detected result, there may be employed a method of detecting with the device 1 only the light from a particle-to-be-observed and light-emitting probe combination or a light-emitting probe having bound to a particle to be observed by utilizing the effect of a fluorescence energy transfer phenomenon using at least two kinds of fluorescent dyes so that the emission of light from the light-emitting probe has not bound to a particle to be observed will be prevented, or so that the wavelength of the light from a particle-to-be-observed and light-emitting probe combination or a light-emitting probe having bound to a particle to be observed and the wavelength of the light from a single light-emitting probe or a light-emitting probe having not bound to a particle to be observed will be made different from one another. For example, the manners using the fluorescence energy transfer phenomenon may be as follows:

Example 1

For the structure using the fluorescence energy transfer phenomenon, the fluorescence quenching may be used. Concretely, as schematically shown in FIG. 3B, after formation of the particle-to-be-observed and light-emitting probe combination, a substance binding to a single light-emitting probe or a light-emitting probe having not bound to a particle to be observed, but not binding to a particle and light-emitting probe combination, and also absorbing the light emitted by the light-emitting probe through the fluorescence energy transfer (Light acceptor) is added in a sample solution, and the substance is made bind only to the light-emitting probe having not bound to the particle to be observed or the single light-emitting probe in a sample solution. Then, when the sample solution in which the light acceptor has been mixed so is observed with the optical analysis device 1, the light is emitted from the light-emitting probe in the particle and light-emitting probe combination, which light is detected with a photodetector, and the light emitted from the single light-emitting probe or the light-emitting probe having not bound to the particle to be observed, to which probe the light acceptor has bound, is absorbed by the light acceptor, and accordingly, the light from the single light-emitting probe or the light-emitting probe having not bound to the particle to be observed is quenched so that the light will not be reflected in a detected result. For such an example, for instance, in a case that a fluorescently labeled nucleic acid or nucleic acid analogue is used as a light-emitting probe for a particle to be observed of a nucleic acid or a nucleic acid analogue, after the binding of a light-emitting probe to a particle to be observed, it becomes possible to quench the fluorescence of the light-emitting probe having not bound to the particle to be observed by adding, as a light acceptor, a nucleic acid or a nucleic acid analogue having a light acceptor site which absorbs light of a fluorescent label of the light-emitting probe and has a base sequence complementary to the light-emitting probe so that the light acceptor will bind to the light-emitting probe, Example 2

As a light-emitting probe, there may be employed a substance having an energy donor site and an energy acceptor site, which substance is designed so that the distance between the energy donor site and the energy acceptor site will change when the light-emitting probe binds a particle to be observed. As an example of such light-emitting probes, for instance, there can be raised Molecular beacon, namely, a nucleic acid molecule, as schematically drawn on FIG. 3D, to which two dyes each to be an energy donor and an energy acceptor in the fluorescence energy transfer phenomenon are attached. In such a molecular beacon, when it is a single molecule (FIG. 3D left), the added dyes are close to one another so that the fluorescence energy transfer phenomenon will occur in the irradiation of the excitation light for the energy donor, and accordingly, the light emitted by the energy donor is transferred to the energy acceptor and quenched, or the light of the emission wavelength of the dye of the energy acceptor (the light of wavelength 2) is emitted; but, when the molecular beacon binds to a particle to be observed (nucleic acid or nucleic acid analogue) (FIG. 3D right), the distance between the two dyes becomes long, and thus, no fluorescence energy transfer phenomenon occurs in the irradiation of the excitation light for the energy donor, resulting in the emission of the light of the emission wavelength of the energy donor (the light of wavelength 1). Therefore, in observation, by detecting selectively only the light of the emission wavelength of the energy donor of the molecular beacon, it becomes possible to detect a particle to be observed even in the presence of a single molecular beacon in a sample solution. Moreover, as a similar principle, a scorpion probe may be used. In this regard, on the contrary to the illustrated example, there may be used a light-emitting probe which is designed such that no fluorescence energy transfer phenomenon occurs in a single light-emitting probe (or a light-emitting probe having not bound to a particle to be observed) while a fluorescence energy transfer phenomenon occurs in a particle and light-emitting probe combination (In that case, the light of the emission wavelength of an energy acceptor is detected selectively). Further, a light-emitting probe may be not only a nucleic acid or a nucleic acid analogue, but also, a substance having at least two light-emitting sites in which the distance between the at least two light-emitting sites changes when the substance binds to or associates with a particle to be observed, resulting in the change of the wavelength of the emitted light.

Example 3

As schematically shown in FIG. 3E, a first probe (light-emitting probe 1) to be an energy donor and a second probe (light-emitting probe 2) to be an energy acceptor are each prepared as light-emitting probes, and added into a sample solution. Then, both the light-emitting probe 1 and the light-emitting probe 2 bind to a particle to be observed to form a combination, and when the light which excites the light-emitting probe 1 is irradiated in this condition, the fluorescence energy transfer phenomenon occurs within the combination so that the light of the emission wavelength (wavelength 2) of the light-emitting probe 2 will be emitted from the combination. On the other hand, from the light-emitting probe 1 having not bound to a particle to be observed, the light of its emission wavelength (wavelength 1) is emitted, and the light-emitting probe 2 having not bound to a particle to be observed, not substantially excited, emits no light. Accordingly, in the system of FIG. 3E, through making the light-emitting probe 1 emit light, the light of the emission wavelength of the light-emitting probe 2 is emitted only from the combination, and therefore, by detecting selectively the light of the emission wavelength of the light-emitting probe 2, it becomes possible to detect a particle to be observed with high accuracy, without removing a light-emitting probe physically out of a sample solution.

Example 4

In a case that a particle to be observed has a light-emitting site, a substance which functions as an energy donor to the light-emitting site of the particle to be observed may be chosen as a light-emitting probe. In that case, as schematically described to FIG. 3F, while the light (wavelength 1) of the emission wavelength is emitted from a single light-emitting probe, the light emitted from the light-emitting probe is absorbed by the light-emitting site of the particle to be observed in the particle to be observed to which the light-emitting probe bound, and then the light (wavelength 2) of the emission wavelength of the light-emitting site of the particle to be observed is emitted. Thus, by making a light-emitting probe emit light and detecting selectively the light of the emission wavelength of the light-emitting site of the particle to be observed, it becomes possible to detect the particle to be observed with high accuracy without removing a light-emitting probe physically out of a sample solution. As such an example, for instance, in a case that a particle to be observed is a nucleic acid, an arbitrary fluorescently labeled substance which gives energy to guanine in the nucleic acid (guanine becomes the energy acceptor) when it binds to nucleic acid may be chosen as a light-emitting probe. Moreover, in a case that a particle to be observed is a protein, an arbitrary labeled substance which gives energy to a tryptophan in the protein (i.e., the tryptophan becomes the energy acceptor) when it binds to the protein may be chosen as a light-emitting probe.

Example 5

In a case that a particle to be observed has a light-emitting site, a substance which functions as an energy acceptor for the light-emitting site of the particle to be observed may be chosen as a light-emitting probe. In that case, as schematically described to FIG. 3G, in a particle to be observed to which a light-emitting probe has bound, the light-emitting probe absorbs the light emitted from the light-emitting site of the particle to be observed so that the light of the emission wavelength (wavelength 2) of the light-emitting probe will be emitted, while the single light-emitting probe emits no light. Thus, by making the light-emitting site of a particle to be observed emit light and detecting the light of the emission wavelength of the light-emitting probe selectively, it becomes possible to detect the particle to be observed with high accuracy, without removing a light-emitting probe physically out of a sample solution.

(iv) Application for the Measurement Accompanied by the Decomposition Reaction of a Particle to be Observed or a Light-Emitting Probe By the way, in the field of research of the base sequence, structure or characteristics of nucleic acid, there is known an experimental method using, as a probe for searching for a base sequence of a nucleic acid, a nucleic acid molecule having an energy donor site and an energy acceptor site where a fluorescence energy transfer phenomenon occurs, and being designed to be decomposed by a predetermined decomposition reaction in a condition that it has bound to a nucleic acid having the complementary base sequence. In such an experimental method, briefly, first, the above-mentioned probe is added to a sample to be tested, and if a nucleic acid including a base sequence complementary to the base sequence of the probe is present in the sample, the probe will bind to the nucleic acid (see the left drawing of FIG. 3H). In this condition, if a predetermined decomposition reaction is progressed, only the probe having bound to the nucleic acid, or both the probe and the nucleic acid are decomposed, so that the energy donor site and energy acceptor site on the probe will separate apart (see the right drawing of FIG. 3H), and accordingly, no fluorescence energy transfer phenomenon will occur, resulting in that the light (wavelength 1) from the energy donor site becomes observable. On the other hand, if no nucleic acid including a base sequence complementary to the base sequence of a probe is present in the sample, the probe does not bind to a nucleic acid, and the probe is not decomposed even if the predetermined decomposition reaction is conducted, and therefore, on the probe, the light from the energy donor site is absorbed by the energy acceptor site and not emitted to the outside. Namely, in the above-mentioned experiment, in accordance with whether or not the light from an energy donor site is detected, it can be detected whether or not a nucleic acid to be observed is present in a sample.

The inventive method may be used in an experiment which uses a light-emitting probe in which a fluorescence energy transfer phenomenon occurs as described above, and which will be decomposed by a predetermined decomposition reaction when it has bound to a particle to be observed (for example, a nucleic acid). In that case, the light detected in the device is light emitted from the light-emitting probe decomposed after binding to the particle to be observed. As examples of such experimental methods, there are raised as follows, for instance:

(a) A method in which a light-emitting probe of a DNA having an energy donor site and an energy acceptor site in which a fluorescence energy transfer phenomenon occurs is added to a sample solution containing a nucleic acid or a nucleic acid analogue to be tested (a particle to be observed), and it is detected whether or not the light-emitting probe is decomposed by a DNA polymerase having a 5'-3' exonuclease activity (Taqman method);

(b) A method in which a light-emitting probe of a DNA having an energy donor site and an energy acceptor site in which a fluorescence energy transfer phenomenon occurs and partially including RNA is added to a sample solution containing a nucleic acid or a nucleic acid analogue to be tested (a particle to be observed), and it is detected whether or not the light-emitting probe is decomposed by an RNaseH (Cycleave method);

(c) A method in which a light-emitting probe of a DNA having an energy donor site and an energy acceptor site in which a fluorescence energy transfer phenomenon occurs and partially including a restriction enzyme identifying region is added to a sample solution containing a nucleic acid or a nucleic acid analogue to be tested (a particle to be observed), and it is detected whether or not the light-emitting probe is decomposed by a restriction enzyme;

(d) A method in which a light-emitting probe of a DNA having an energy donor site and an energy acceptor site in which a fluorescence energy transfer phenomenon occurs is added to a sample solution containing a nucleic acid or a nucleic acid analogue to be tested (a particle to be observed), and it is detected whether or not the light-emitting probe is decomposed by an exonuclease which decomposes specifically a double strand nucleic acid.

When these experiments are performed using the inventive method, a sample solution in each experiment may be prepared in an usual manner. The wavelength of the light which should be detected in Measurement of light intensity, as described in detail later, is the wavelength of the light emitted after the decomposition of the light-emitting probe. Moreover, the detected particle count is primarily the number of the decomposed light-emitting probes, which number will be equal to the number of the molecules of the nucleic acids or nucleic acid analogues to which the light-emitting probes have bound.

(2) Measurement of the Light Intensity of a Sample Solution

The measurement of the light intensity in the inventive optical analysis may be performed in the same manner as the measurement process of the light intensity in FCS or FIDA except driving the mirror deflector 17 to move the position of the light detection region within the sample solution (to scan in the sample solution) during the measurement. In the operation process, typically, after dispensing a sample solution into the well(s) 10 of the micro plate 9 and putting it on the stage of the microscope, when a user inputs to the computer 18 a command of a measurement start, the computer 18 executes programs memorized in a storage device (not shown)(the process of changing the optical path in order to move the position of the light detection region in the sample solution, and the process of detecting light from the light detection region during the moving of the position of the light detection region), and then illuminating the light detection region in the sample solution with the excitation light and measuring light intensity will be started. During this measurement, under the control of the operation process of the computer 18 according to the programs, the mirror deflector 17 drives the mirror 7 (galvanomirror) to move the position of the light detection region in the well 10, and simultaneously with this, the photodetector 16 sequentially converts the detected light into an electric signal and transmits it to the computer 18, which generates the time series light intensity data from the transmitted light signals and store it in an arbitrary manner. In this regard, the photodetector 16 is typically a super high sensitive photodetector which can detect an arrival of a single photon, and thus the detection of light may be the photon counting performed in the manner of measuring sequentially the number of photons which arrive at the photodetector for every predetermined unit time (BIN TIME), for example, every 10 µs, during a predetermined time, where the time series light intensity data will be a time series photon count data.

The moving speed of the position of the light detection region during the measurement of the light intensity may be a predetermined velocity set arbitrarily, for example, experimentally or in order to meet the purpose of an analysis. In a case of acquiring the information on the number density or concentration based on the number of detected particles to be observed, the region size or volume through which the light detection region has passed is required, and therefore, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

Figure 4A:
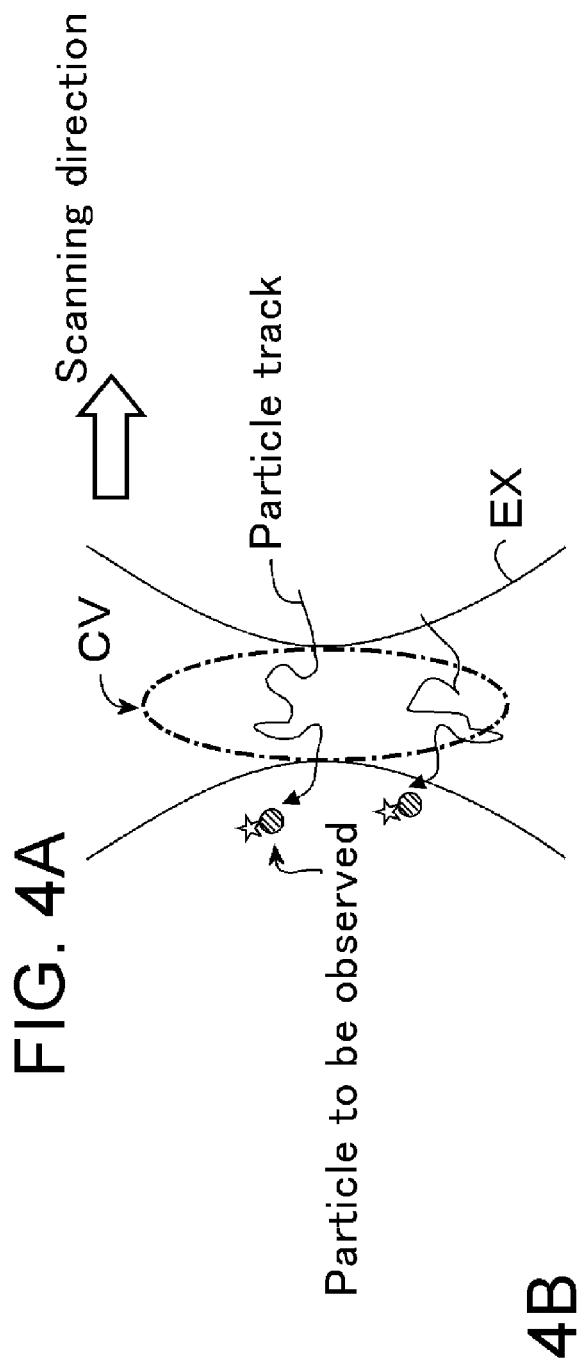
FIGS. 4A and 4B are a drawing of a model in the case that a particle to be observed crosses a light detection region owing to Brownian motion and a diagram showing the example of the variation of the photon counts (light intensity) with time in this case, respectively.
Figure 4B:
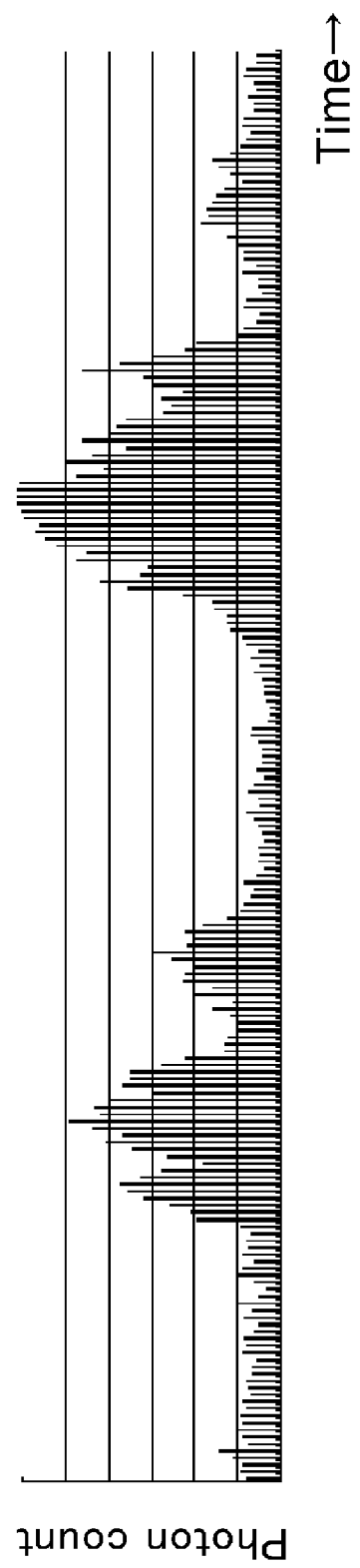

By the way, regarding the moving speed of the position of the light detection region, in order to perform quantitatively precisely individual detection of a particle to be observed from the measured time series light intensity data or the counting of the number of particles to be observed, it is preferable that the moving speed is set to a value quicker than the moving speed in the random motion, i.e., Brownian motion of a particle to be observed (more strictly, a particle and light-emitting probe combination or a light-emitting probe having been decomposed and liberated after the binding to a particle). Since the particle to be observed in the inventive optical analysis technique is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 4A, whereby the light intensity changes at random as shown in FIG. 4B (As already noted, the excitation light intensity in the light detection region is reduced from the peak at the center of the region toward its outside), so that it becomes difficult to determine a significant light intensity change corresponding to each particle to be observed. Then, preferably, as drawn in FIG. 5A, the moving speed of the position of the light detection region is set to be quicker than the average moving speed of a particle by the Brownian motion (diffusional moving velocity) so that a particle will cross the light detection region in an approximately straight line and thereby the profile of the change of the light intensity corresponding to each particle becomes almost uniform in the time series light intensity data as illustrated in FIG. 5B (When a light-emitting particle passes through the light detection region in an approximately straight line, the profile of the light intensity change is similar to the excitation light intensity distribution) and the correspondence between each particle to be observed and light intensity can be easily determined.

Concretely, the time Δt required for a particle to be observed (more strictly, a particle and light-emitting probe combination or a light-emitting probe having been decomposed and liberated after the binding to a particle) having a diffusion coefficient D to pass through the light detection region of radius Wo (confocal volume) by Brownian motion is given from the expression of the relation of mean-square displacement:

$$(2Wo)^2 = 6D \cdot \Delta t \tag{1}$$

as:

$$\Delta t = (2Wo)^2 / 6D \tag{2},$$

and thus, the velocity of the particle to be observed moving by Brownian motion (diffusional moving velocity) Vdif, becomes approximately $$Vdif = 2Wo/\Delta t = 3D/Wo \tag{3}$$

Then, with reference to this, the moving speed of the position of the light detection region may be set to a value sufficiently quicker than Vdif. For example, when the diffusion coefficient of a particle to be observed is expected to be about $D = 2.0 \times 10^{-10}$ m$^2$/s, Vdif will be $1.0 \times 10^{-3}$ m/s, supposing Wo is about 0.62 μm, and therefore, the moving speed of the position of the light detection region may be set to its 10 times or more, e.g. 15 mm/s, etc. In this regard, when the diffusion coefficient of a particle to be observed is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

(3) Analysis of Light Intensity

When the time series light intensity data of a sample solution are obtained by the above-mentioned processes, an analysis of the light intensity as described below may be performed in the computer 18 through processes in accordance with programs memorized in a storage device.

(i) Detection of One Particle to be Observed

When the track of one particle to be observed in its passing through the light detection region is approximately straight as shown in FIG. 5A, the light intensity variation corresponding to the particle to be observed in the time series light intensity data has a profile reflecting the light intensity distribution in the light detection region (determined by the optical system) (usually approximately bell shape) as schematically drawn in FIG. 7A. Then, in one of the methods for the detection of a particle to be observed, a threshold value Io is set for the light intensity, and when the time width Δτ for which the light intensity exceeding the threshold value continues is in a predetermined range, the profile of the light intensity may be judged to correspond to one particle having passed through the light detection region, and thereby one particle to be observed is detected. The threshold value Io for the light intensity and the predetermined range for the time width Δτ are determined based on a profile expected in the intensity of the light emitted from a particle-to-be-observed and light-emitting probe combination (or a light-emitting probe having been decomposed and separating after the binding to a particle) moving relatively to the light detection region at a predetermined speed, and their concrete values may be set arbitrarily or experimentally, and also may be selectively determined depending upon the characteristics of a particle-to-be-observed and light-emitting probe combination (or a light-emitting probe having been decomposed and separating after the binding to a particle).

Moreover, in another method of detection of a particle to be observed, when the light intensity distribution in the light detection region can be assumed as Gaussian distribution:

$$I = A \cdot \exp(-2r^2/a^2) \tag{4},$$

and when the intensity A and the width a, computed by fitting the expression (4) to the profile of a significant light intensity (a profile which can be clearly judged not to be a background), are within the respective predetermined ranges, the profile of the light intensity may be judged to correspond to one particle to be observed having passed through the light detection region, and thereby the detection of one particle to be observed will be done. However, the profile with the intensity A and the width a out of the predetermined ranges may be ignored as a noise or a contaminant in the analysis.

(ii) The Counting of Particles to be Observed

The counting of particles to be observed may be done by counting in an arbitrary way the number of the particles detected by the above-mentioned method of detection of a particle to be observed. However, for the large number of particles, for example, it may be accomplished by the processes illustrated in FIG. 6 and FIG. 7B.

Referring to FIG. 6 and FIG. 7B, in one example of ways of performing the counting of particles from the time series light intensity (photon counts) data, after the measurement of the light intensity as explained above, namely, performing the scanning in the sample solution with the light detection region and the photon counting to acquire time series light signal data (photon count data)(Step 100), to these time series light signal data (FIG. 7B, the upper row "detected result (unsettled)"), a smoothing treatment is performed (step 110, FIG. 7B mid-upper row "smoothing"). Although the light emitted by a particle and light-emitting probe combination or a light-emitting probe is stochastic so that gaps will be generated in data values in minute time, such gaps in the data value can be disregarded by the smoothing treatment. The smoothing treatment may be done for example by the moving average method. In this regard, parameters in performing the smoothing treatment, e.g., the number of datum points in one time of the averaging, the number of times of a moving average, etc. in the moving average method, may be suitably set in accordance with the moving speed (scanning speed) of the position of the light detection region and/or BIN TIME in the light signal data acquisition.

Next, on the time series light signal data after the smoothing treatment, in order to detect a time domain (pulse existing region) in which a significant signal exists, the first differentiation value with time of the time series light signal data after the smoothing treatment is computed (step 120). As illustrated in FIG. 7B, the mid-low row "time differential", in the time differential value of time series light signal data, the variation of the value increases at the time of the signal value change, and thereby, the start point and the end point of a significant signal (pulse signal) can be determined advantageously by referring to the time differential value.

After that, a significant signal (pulse signal) is detected sequentially on the time series light signal data, and it is judged whether or not the detected pulse signal is a signal corresponding to a particle to be observed. Concretely, first, on the time series time-differential value data of the time series light signal data, the starting point and the end point of one pulse signal are searched and determined by referring to the time differential value sequentially, so that a pulse existing region will be specified (step 130). When one pulse existing region has been specified, the fitting of a bell-shaped function is applied to the smoothed time series light signal data in the pulse existing region (FIG. 7B, the lower row "bell-shaped function fitting"), and then, parameters in the bell-shaped function, such as the peak intensity, Imax; the pulse width (full width at half maximum), w; the correlation coefficient in the fitting (of the least square method), etc. are computed (step 140). In this regard, although the bell-shaped function to be used in the fitting is typically Gauss function, it may be Lorentz type function. And it is judged whether or not the computed parameters of the bell-shaped function are within the respective ranges assumed for the parameters of the bell-shaped profile drawn by a light signal detected when one particle and light-emitting probe combination or one light-emitting probe passes a light detection region, i.e., whether or not each of the peak intensity, the pulse width and the correlation coefficient is within the corresponding predetermined range (step 150). Thus, the signal, whose computed parameters of the bell-shaped function are judged to be within the ranges assumed in a light signal corresponding to one particle and light-emitting probe combination or a light-emitting probe, as shown in FIG. 8 left, is judged as a signal corresponding to one particle to be observed, and thereby, one particle to be observed has been detected, and one particle is counted (The number of particles is counted up. Step 160). On the other hand, a pulse signal, whose computed parameters of the bell-shaped function are not within the assumed ranges, as shown in FIG. 8 right, is disregarded as noise.

The search and the judgment of a pulse signal in the processes of the above-mentioned steps 130-160 are repetitively carried out in the whole region of the time series light signal data, and whenever one particle to be observed is detected, it is counted as one particle. And, when the search of the pulse signal in the whole region of the time series light signal data is completed (step 170), the count value of particles obtained till then is considered as the number of particles to be observed which have been detected in the time series light signal data.

(iii) Determination of the Number Density or Concentration of a Particle to be Observed When the counting of particles to be observed has been done, the number density or concentration of the particle to be observed can be determined using the volume of the whole region which the light detection region has passed through during the acquisition of the time series light signal data. However, the effective volume of the light detection region varies depending on the wavelength of excitation light or detected light, the numerical aperture of lenses and the adjustment condition of the optical system, and therefore, it is generally difficult to compute the effective volume of the light detection region from the design parameter values, and it is not easy to compute the whole volume which the light detection region has passed through, either. Then, typically, the light intensity measurement, the detection of light-emitting particles and the counting thereof are performed as explained above with a solution having a known particle concentration (reference solution) under the same condition as that for the measurement of a sample solution to be tested, and then, from the detected number of particles and the concentration of particle in the reference solution, the volume of the whole region which the light detection region has passed through, i.e., the relation between the detected number and the concentration of the particle to be observed, may be determined. Preferably, the particle of a reference solution may be a light emitting label (fluorescent dye etc.) having the same wavelength characteristic as a particle and light-emitting probe combination that a particle to be observed forms (or light-emitting probe having been separated from a particle to be observed after having bound thereto). Concretely, for example, supposing the detected number of the particles is N in a reference solution of the particle concentration C, the volume Vt of the whole region which the light detection region has passed through is given by:

$$Vt = N/C \quad (5).$$

Alternatively, the plurality of solutions of different concentrations are prepared as reference solutions and the measurement is performed for each of the solutions, and then, the average value of the computed Vt is determined as the volume Vt of the whole region which the light detection region has passed through. Thus, when Vt is given, the number density c of the particle of the sample solution, whose counting result of the particles is n, is given by:

$$c = n/Vt \quad (6)$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage apparatus of the computer 18 the information on the relations (expression (5)) between concentrations C and particle numbers N of various standard particles for assumed moving patterns of the light detection region, so that a user of the device can appropriately use the memorized information on the relation in conducting an optical analysis.

In order to verify the validity of the present invention explained above, the experiments described below were conducted. In this regard, it should be understood that the following embodiments illustrate the validity of the present invention only, not intended to limit the scope of the present invention.

Embodiment 1

Measurement of Nucleic Acid Concentration Using a Fluorescent Dye

Using SYTOX Orange, which is an intercalator fluorescent dye of DNA (a dye of which fluorescence intensity increases notably when it binds to DNA) as a light-emitting probe, the measurable range of concentration of DNA in a sample solution by the inventive method was verified (see FIG. 3C). In this connection, the measurable range of concentration of DNA from the fluorescence intensity measured with a plate reader was also measured as a control experiment.

As for the samples, there were prepared a plurality of sample solutions by dissolving DNA (pbr322, Takara Bio, Inc., Cat. No. 3035) as the particle to be observed, into a phosphate buffer (including 0.05% Tween20) containing SYTOX Orange (Invitrogen Corp., Cat. No. S-11368) at 10 nM such that the DNA molecule concentration was to be 0M (reference solution), 100 fM, 1 pM, 10 pM or 100 pM. In this regard, SYTOX Orange is a fluorescent dye whose fluorescence intensity increases about 500 times when it binds to DNA (an example of a fluorescent dye whose wavelength characteristic changes in FIG. 3C).

In the measurement in accordance with the inventive method, a single molecule fluorescence measuring apparatus MF-20 (Olympus Corporation), equipped with the optical system of a confocal fluorescence microscope and a photon counting system, was used as the optical analysis device, and time series photon count data were acquired for the above-mentioned respective sample solutions in accordance with the manner explained in the above-mentioned "(2) Measurement of the light intensity of a sample solution". In that time, a 633 nm laser light was used for excitation light, and the detected light wavelength was set from 660 to 710 nm using a band pass filter. The moving speed of the position of the light detection region in the sample solution was set to 15 mm/second; BIN TIME was set to 10 μsec.; and the measurement time duration was set to 2 seconds. After the light intensity measurement, in accordance with the procedures described in the above-mentioned "(3) (ii) The counting of particles to be observed", the light signals detected in the time series data from the time series photon count data acquired for each sample solution were counted. In the smoothing by the moving average method of data in step 110, the data points averaged at once was nine, and the moving average process was repeated 5 times. Moreover, in the fitting of step 140, the fitting of Gauss function to the time series data was carried out by the least square method, and a peak intensity, a pulse width (full width at half maximum) and a correlation coefficient (in the gauss function) were determined. Furthermore, in the decision process of step 150, only the pulse signal satisfying the following conditions:

20 μsec.<pulse width<400 μsec.

Peak intensity>1 (photon/10 μsec.)

Correlation coefficient>0.95    (A)

was judged as a light signal corresponding to a particle to be observed, while a pulse signal which did not satisfy the above-mentioned conditions was disregarded as noise, and then, the number of the signals judged as a light signal corresponding to a particle to be observed was counted as the "pulse number".

In the control experiment, fluorescence intensity was measured for each of the above-mentioned sample solutions using a plate reader SH-8000lab (Corona). The excitation light wavelength was set to 543 nm; the detected light wavelength, to 570 nm; and both the band widths of the excitation and detection sides, to 12 nm. In measuring the fluorescence intensity, 3 times of measurement where 50 times of excitation light flash were applied were performed, and their average was used as the final fluorescence intensity value.

FIGS. 9A and 9B each show the measurement results (pulse number) by the above-mentioned inventive method and the measurement results (fluorescent intensity) in the control experiment, detected in the sample solutions of the respective concentrations. Referring to FIG. 9A first, the pulse number measured by the inventive method (the number of the light signals counted) increased almost in proportion to the nucleic acid concentration. According to this result, it has been found that the inventive method enables detecting individual nucleic acids (particle to be observed) one by one, and that, by counting individual particles to be observed according to the inventive method, its concentration can be determined quantitatively.

Further, while no significant difference between the fluorescence intensity in the case of the nucleic acid concentration of 0 M and the fluorescence intensity in the case of the nucleic acid concentration of 100 pM can be recognized in the control experiment of FIG. 9B, the significant difference was seen between the pulse number in the case of the nucleic acid concentration of 0 M and the pulse number in the case of the nucleic acid concentration of 100 fM in the inventive method of FIG. 9A. The reason of these results is considered as follows: On the fluorescence intensity measured with the plate reader, the light signals owing to noises or contaminants were superposed and accordingly the S/N ratio got worse in the low concentration range where the contribution of noises or contaminants to the fluorescence intensity is relatively large. On the other hand, in the case of the present invention, it was judged whether or not each pulse signal in time series light signal data corresponded to a particle to be observed, and signals judged as noises or contaminants were disregarded (see FIG. 8), and therefore even in the low concentration region where the contribution of noises or contaminants to the fluorescence intensity is large relatively, the S/N ratio was maintained to be comparatively good. Thus, it has been shown that, according to the inventive method, the number density or concentration of a particle can be determined to the concentration range lower than the limit of the number density or concentration measurable by conventional methods using fluorescence intensity. Further, while the lower limit of the particle concentration measurable in optical analysis techniques, such as FCS, FIDA, and PCH, including statistical procedures, e.g. calculation of fluorescence intensity fluctuation was about 1 nM, the lower limit of the particle concentration measurable in the present embodiment was ~100 fM, and accordingly, it has been also shown that, according to the present invention, the measurement is possible for a particle in the range of a concentration significantly lower than the case of the optical analysis techniques such as FCS, FIDA and PCH.

By the way, with reference to the higher concentration side in the result of FIG. 9, while the pulse number was about 10 times increased expectedly in the increase of the concentration from 10 pM to 100 pM in the case of the present invention, the increase width of fluorescence intensity in the increase of the concentration from 10 pM to 100 pM was smaller than the expected 10 times in the control experiment. This phenomenon can be considered as follows: In the system of the present embodiment, as illustrated in FIG. 9C left, two or more fluorescent dyes bind together to a nucleic acid of a particle to be observed. In that case, when the nucleic acid concentration is lower than the fluorescent dye concentration, a plenty of dyes are present, and thus the number of dyes having bound to one nucleic acid is stable, but when the nucleic acid concentration is higher, the number of the dyes becomes relatively short and the number of dyes having bound to one nucleic acid is reduced as illustrated in FIG. 9C right, and therefore it can be considered that the fluorescence intensity did not easily increase following the nucleic acid concentration. On the other hand, since the present invention is designed so that the number of light signals corresponding to a particle to be observed may be counted, the influence due to the reduction of the number of dyes having bound to one nucleic acid is small, and thus, it can be considered that the pulse number expectedly increased to the higher concentration range. This shows that, according to the inventive method, in a system where two or more light-emitting probes bind to a particle to be observed, the number density or concentration of the particle can be determined up to a concentration range higher than the upper limit of the number density or concentration measurable under the assumption that the fluorescence intensity is proportional to the number density or concentration of light-emitting particles in the prior art.

Embodiment 2

Detection of a Nucleic Acid Using a Molecular Beacon

It is verified that a nucleic acid molecule having a specific base sequence is detectable using a molecular beacon according to the inventive method. As already noted, the molecular beacon is a nucleic acid molecule in which a donor dye and an acceptor dye have been added to its both ends, respectively, and the molecule is designed such that, in a single molecule, the distance between the donor dye and acceptor dye are so close that a fluorescence energy transfer phenomenon from the donor dye to the acceptor dye can occur, but, when it binds to a nucleic acid or a nucleic acid analogue having a base sequence complementary to its own base sequence, the distance between the donor dye and acceptor dye increases so that no fluorescence energy transfer phenomenon will occur (see FIG. 3D).

In the experiment, as the molecular beacon, there was used a nucleic acid having the following base sequence in which TAMRA (donor dye) was attached to 5' end, and BHQ-2 (acceptor dye, in this case, fluorescence was hardly emitted) was added to 3' end:

```
TAMRA-cctacgccaacagctccaactacgtagg-BHQ2
```

Also, for the particle to be observed, the nucleic acid having the following base sequence was used:

```
gtagttggagctgttggcgtaggcaagagtgccttgacgatacagctaa
ttcag
```

The above-mentioned nucleic acids were compounded by requesting Sigma genosis, Inc. Then, to prepare the sample solution, the above-mentioned molecular beacon and particle to be observed (nucleic acid) were dissolved at 500 pM and 100 nM, respectively, in a phosphate buffer (Tween 20 including 0.05%). For a control solution, there was prepared a solution containing only a molecular beacon at 500 µM without the particle to be observed (nucleic acid).

Measurements for the sample solution and control solution by the inventive method were conducted on the same conditions as the case of Embodiment 1. Also, as a control experiment, the fluorescence intensities of the sample solution and control solution were measured similarly to the case of Embodiment 1, using the plate reader, where the excitation light wavelength was set to 550 nm, and the detected light wavelength was set to 576 nm.

FIGS. 10A and 10B each show the measurement results (pulse number) detected by the above-mentioned inventive method and the measurement results (fluorescence intensity) by a control experiment for the sample solution (MB+Target) and the reference solution (only MB). First, as clearly seen with reference to FIG. 10A, the pulse number of the sample solution containing the particle to be observed of the nucleic acid notably increased as compared with the case of the control solution (6 times difference), and the variances were also small. On the other hand, in the case of the control experiment in FIG. 10B, the difference was seen in the averages of the fluorescence intensity between the sample solution and the control solution, but the variances were large. The concentration of the molecular beacon in the present embodiment was 500 pM as noted, and considering that that concentration is close to the lower limit of the concentration measurable from the fluorescence intensity using a plate reader as understood from the result of Embodiment 1, the results of FIG. 10 shows that, according to the inventive method, the detection of a nucleic acid having a certain specific base sequence using a molecular beacon can be achieved also in a solution of a low light-emitting probe concentration in better accuracy, as compared with the case of the conventional detection method based on fluorescence intensity.

Embodiment 3

Detection of a Nucleic Acid in a Sample Solution from which Unreacted Fluorescence-Labeled Probes have been Removed by Physical Purification It was verified that, after combining a fluorescently labeled short nucleic acid (fluorescently labeled probe) as a light-emitting probe with a nucleic acid (target nucleic acid) to be a particle to be observed, the target nucleic acid was detectable in the sample solution obtained by removing the unreacted fluorescence-labeled probes through a physical purification procedure according to the inventive method. (see FIG. 3A)

Concretely, a specimen (Probe-Target) was prepared by applying the annealing process (annealing temperature: 95° C., 90° C., 80° C., 70° C., 60° C., 50° C., 40° C., 30° C., 20° C., each for 10 min.–0.1° C./sec.) to a solution obtained by mixing target nucleic acids and fluorescence-labeled probes at a ratio of 100 pM:10 nM into STE buffer solution (200 mM NaCl, 10 nM Tris, 1 nM EDTA, pH=7.0), and a specimen (Probe) was prepared by similarly applying the annealing process to a solution obtained by dissolving fluorescence-labeled probes in the STE buffer solution at 10 nM. The base sequences of the used target nucleic acid and fluorescence-labeled probe are as follows:

```
Target nucleic acid:
5'-gaaacagctatgaccatgattacgccaagcttgcatgcctgcagg tcgactctagaggatccccgggtaccgagctcgaattcactggccgtc gttttac-3'

Fluorescence-labeled probe:
ATTO647N-ggggatcctctagagtcgacc
(ATTO647N is a fluorescent dye.)
```

After that, parts of those specimens were purified using silica gel membrane (purification kit of QIAGEN (MinElute PCR Purification kit)), and eluted with 50 µL of the STE buffer solution. Then, in accordance with the inventive method, the measurement of light and the detection of the pulse signals were performed under the same conditions as the case of the embodiment 1, each for the specimen purified with the silica gel membrane (purified), and the specimen not refined (not purified) as the sample solutions. In this regard, a 100 µW laser light was used for the excitation light, and the measurement with the light measuring time for 20 seconds was performed 3 times.

FIG. 11 shows the average (bar graph) and standard deviation (error bar) of the pulse number detected in each specimen. As understood from the drawing, while, in the not purified specimens (not purified), little difference in the pulse number was seen between the case containing target nucleic acids (Probe-Target) and the case containing no target nucleic acid (Probe), the pulse number in the case containing no target nucleic acids (Probe) was substantially reduced as compared with the case containing the target nucleic acids (Probe-Target) in the purified specimens (purified). That is, this shows that, by removing unreacted light-emitting probes through physical purification (purification with silica gel membrane), it becomes possible to detect a particle to be observed selectively.

Embodiment 4

Detection of a Nucleic Acid Using Fluorescence Energy Transfer (FRET)

It was verified that, under the condition that two kinds of fluorescently labeled short nucleic acids (donor peptide nucleic acid, acceptor peptide nucleic acid), which cause the fluorescence energy transfer when they are mutually in close proximity to one another, as light-emitting probes, were made bind to a particle to be observed of a nucleic acid (target nucleic acid), and then, light acceptors (quenching probe), which specifically bind to the unreacted light-emitting probes, were made combine to the unreacted light-emitting probes so as to quench the light from the fluorescent labels of the unreacted light-emitting probes, the target nucleic acid was selectively detectable by detecting the light from the acceptor peptide nucleic acid (the light-emitting probe used as an energy acceptor) and the concentration of the target nucleic acid was determinable (see FIGS. 3B and 3E) when a fluorescence energy transfer phenomenon between the donor peptide nucleic acid and acceptor peptide nucleic acid on the target nucleic acid was made to occur (see FIG. 12A).

Concretely, there were prepared sample solutions (10 mM Tris-HCl (pH 8.0)) containing 0.1% Pluronic F-127, where fluorescence energy donor peptide nucleic acid (PANAGENE) and acceptor peptide nucleic acid (PANAGENE) were added so as to be at 200 pM, respectively, and target nucleic acids (SIGMA GENOSYS) were added to be 1 pM, 10 pM or 100 pM. A sample containing no target nucleic acid was also prepared. Then, after the denaturalization of each sample solution by heating for 5 minutes at 95° C., the associations of the target nucleic acids and peptide nucleic acids were formed by reducing the liquid temperature gradually to 20° C. (the temperature lowering speed was set to 0.1° C./sec., and the temperature lowering treatment were performed at 90° C. for 5 minutes; at 80° C. for 10 minutes; at 70° C. for 10 minutes; at 60° C. for 10 minutes; at 50° C. for 10 minutes; at 40° C. for 10 minutes; and at 30° C. for 10 minutes). After this, quenching probes for the donor peptide nucleic acid (SIGMA GENOSYS) and quenching probes for the acceptor peptide nucleic acid (SIGMA GENOSYS) were added to be at 1 nM, respectively, and the incubation was carried out for 30 minutes at 20° C. The base sequences of the donor peptide nucleic acid, acceptor peptide nucleic acid, nucleic acid for quenching the donor peptide nucleic acid, nucleic acid for quenching the acceptor peptide nucleic acid, and target nucleic acid are as follows, respectively:

```
Donor peptide nucleic acid:
Alexa488-OO-cctacgccaccagctccaac

Acceptor peptide nucleic acid:
agctgtatcgtcaaggcact-O-Lys-Alexa594

Quenching probe for donor peptide nucleic acid:
ggagctggtggcg-BHQ1-dT-agg-BHQ1

Quenching probe for acceptor peptide nucleic acid:
BHQ2-ag-BHQ2-dT-gccttgacgataca Target nucleic acid:
atgactgaatataaacttgtggtagttggagctggtggcgtaggcaaga gtgccttgacgatacagctaattcagaat
```

In the target nucleic acid, the left underline is a sequence binding to the donor peptide nucleic acid, and the right underline is a sequence binding to acceptor peptide nucleic acid.

Alexa488 and Alexa594 are fluorescent dyes, and BHQ1 and BHQ2 are the quenching molecules for Alexa488 and Alexa594, respectively.

Next, using the above-mentioned sample solutions, the measurement of light, the detection and counting of the pulse signals were performed in accordance with the inventive method. In the measurement, a single molecule fluorescence measuring apparatus MF20, equipped with an optical system of a confocal fluorescence microscope and a photon counting system (Olympus, Inc.) was used as the optical analysis device to acquire the time series photon count data for each of the above-mentioned sample solutions. In that case, for the excitation light, a 1-mW laser light of 488 nm (corresponding to the excitation wavelength of the fluorescent dye Alexa488 of the donor peptide nucleic acid) was used and the detected light wavelength was set to 615 nm—(corresponding to the emission wavelength of the fluorescent dye Alexa594 of the acceptor peptide nucleic acid) with a long pass filter. The moving speed of the position of the light detection region in the sample solution was set to 67.5 mm/sec., BIN TIME was set to 10 μsec. and the measuring time was set to 2 seconds. Also, the measurement was performed five times for each sample. After the measurements of the light intensity, the detection and counting of pulse signals were performed on the time series photon count data acquired for each sample solution, similarly to the embodiment 1. And, the averages and standard deviations of those detected pulse numbers were computed.

FIG. 12B shows the averages (bar graphs) and standard deviations (error bars) of the pulse numbers, detected in the sample solutions of the target nucleic acid of the above-mentioned respective concentrations. With reference to the drawing, the pulse number increased with increase of the target nucleic acid concentration in the concentration of 1 pM or more. This shows that, by making two kinds of light-emitting probes causing a fluorescence energy transfer bind to a particle to be observed and detecting the light of the light-emitting probe to be an energy acceptor, the selective detection of the particle to be observed and the determination of the concentration thereof become possible.

Embodiment 5

Detection of a Nucleic Acid (a Particle to be Observed) Using the Fluorescence Quenching Method It was verified that, in accordance with the inventive method, a target nucleic acid was detectable in a sample solution in which, after making fluorescently labeled short nucleic acid (fluorescently labeled probe) as a light-emitting probe bind to a particle to be observed of a nucleic acid (target nucleic acid), a nucleic acid labeled with a fluorescence quenching molecule (quenching probe) was applied to an unreacted fluorescently labeled probe (see FIG. 3B).

Concretely, a single strand nucleic acid whose 5' end was modified with a fluorescent dye, Alexa488 (fluorescent probe), and a single strand nucleic acid whose 3' end was modified with a quenching molecule, BHQ1 (quenching probe), were dissolved to be at 5 nM and 2 μM, respectively, in a 100 mM Tris-HCl (pH 8.0) solution (Tris buffer). Also, similarly, a double strand nucleic acid (target nucleic acid) was dissolved to be at 100 pM, 1 nM and 10 nM in the Tris buffer. Next, 5 μL of the fluorescent probe solution, 5 μL of the quenching probe solution, 5 μL of each target nucleic acid solution and 350, of Tris buffer were mixed. The temperature of these solutions was raised to 95° C. and then lowered to 20°

C. over 90 minutes with a thermal cycler, such that the fluorescent probe was made hybridize with the target nucleic acid. The base sequences of the fluorescent probe, quenching probe, and target nucleic acid are as follows: (described in the direction of 5'→3').

```
Fluorescent probe:
aaacttgtggtagttggagctgttggcgtagg

Quenching probe:
aacagctccaactaccacaagttt

Target nucleic acid:
gaagtacagttcattacgatacacgtctgcagtcaactggaattttcatga ttgaattttgtaaggtattttgaaataattttttcatataaaggtgagtttg tattaaaaggtactggtggagtatttgatagtgtattaaccttatgtgtga catgttctaatatagtcacatttttcattattttttattataaggcctgctga aaatgactgaatataaacttgtggtagttggagctggtggcgtaggcaaga gtgccttgacgatacagctaattcagaatcattttgtggacgaatatgatc caacaatagaggtaaatcttgttttaatatgcatattactggtgcaggacc attctttgatacagataaaggtttctctgaccattttcatgagtacttatt acaagataattatgctgaaagttaagttatctgaaatgtaccttgggtttc aagttatatgtaaccattaatatgggaactttact
```

In the above-mentioned sample solution, since a large amount of the quenching probes was present, all the fluorescent probes not binding to the target nucleic acids bound to the quenching probes so that the fluorescence from the fluorescent probe bound to the quenching probe was to be substantially quenched (see FIG. 13A).

Then, in accordance with the inventive method, the measurement of light, the detection and counting of pulse signals were performed using the above-mentioned sample solution. In the measurement, a single molecule fluorescence measuring apparatus MF20, equipped with an optical system of a confocal fluorescence microscope and a photon counting system (Olympus, Inc.) was used as the optical analysis device to acquire the time series light intensity data (photon count data) for each of the above-mentioned sample solutions. In that case, for the excitation light, a 200 μW laser light of 488 nm was used and the light of the wavelength band of 510 to 560 nm was measured with a band pass filter, and the time series light intensity data were generated. The light detection region in the sample solution was rotated with the moving speed of 15 mm/second, BIN TIME was set to 10 μsec. and the measurement for 2 seconds was conducted 5 times. Then, similarly to the embodiment 1, after smoothing the time series light intensity data obtained by the measurements, the detection of the peak was done through the differentiation. Among the regions which could be regarded to be a pulse signal, the pulses which could be approximated with a gauss function and had the intensity of 1 or more were counted.

The pulse number (the average of the five measurements) obtained from each sample solution is shown in FIG. 13B. As understood from the drawing, the pulse number increased with the increase of the target nucleic acid concentration. In particular, there is no overlapping in the standard deviations of the five measurements between the cases of 0M and 100 pM: This suggests that, according to the method of this embodiment, the measurement of the nucleic acid concentration of 100 pM or more is possible.

Embodiment 6

Detection of a Nucleic Acid Using QUAL Reaction

It was verified that a nucleic acid molecule having a specific base sequence was detectable in accordance with the inventive method using QUAL (Quenched auto-ligation) reaction (nonpatent document 4). As shown in FIG. 14A, in the QUAL reaction, when a single strand nucleic acid in which the 5' end is labeled with a fluorescence molecule (white circle) and a quenching molecule (black circle) being mutually close to each other (E probe—light-emitting probe), and a single strand nucleic acid in which the 3' end is modified with phosphosulfate (N probe) bind onto a single strand nucleic acid having a base sequence to be tested (a target nucleic acid—a particle to be observed) with the 5' end of the E probe and the 3' end of the N probe being close to each other (FIG. 14A the upper row), the E probe and N probe bind to each other (in the drawing, the site designated X) while the quenching molecule on the 5' end is liberated (FIG. 14A the lower row) so that the fluorescence molecule of the 5' end will emit light, and thereby an existence of the nucleic acid having the specific base sequence becomes detectable. That is, this is an example of a reaction in which light-emitting efficiency changes depending on the kind of a particle to be observed (see FIG. 3H).

Concretely, a single strand nucleic acid, which was modified with a quenching molecule Dabcyl at 5' end and with a fluorescence molecule Alexa 488 at t of the third base from the 5' end (E probe, Japan bio-service), and a single strand nucleic acid, which was modified with phosphosulfate at the 3' end (N probe, Japan bio-service), were dissolved in a 100 mM Tris-HCl (pH 8.0) solution to be at 10 nM and 100 nM, respectively. Also, similarly, a single strand nucleic acid (a target nucleic acid) was dissolved in a 100 mM Tris-HCl (pH 8.0) solution to be at 10 pM, 100 pM, 1 nM, and 10 nM, respectively. Then, 3 μL of the E probe solution, 3 μL of the N probe solution, 3 μL of each of the target nucleic acid solutions and 21 μL of the 100 mM Tris-HCl (pH 8.0) solution containing 400 mM NaCl were mixed, and the temperature of these solutions was raised to 95° C. using a thermal cycler, and subsequently, the reaction was made at 50° C. for 1 hour. The base sequences of the E probe, N probe and target nucleic acid are as follows:

```
E probe:
tcttgcctacgccaccagctccaac

N probe:
ttctgaattagctgtatcgtcaaggcac

Target nucleic acid:
gttggagctggtggcgtaggcaagagtgccttgacgatacagctaattc agaa
```

Thus, only when the E probe and N probe bind to the target nucleic acid and the quenching molecule Dabcyl on the E probe is liberated, the light of Alexa488 on the E probe will be detected.

Next, in accordance with the inventive method, the measurement of light, the detection and counting of pulse signals were performed using the above-mentioned sample solutions. In the measurement, a single molecule fluorescence measuring apparatus MF20, equipped with an optical system of a confocal fluorescence microscope and a photon counting system (Olympus, Inc.) was used as the optical analysis device to acquire the time series light intensity data (photon count data)

for each of the above-mentioned sample solutions. In that case, for the excitation light, a 200 μW laser light of 488 nm was used and the light of the wavelength band of 510 to 560 nm was measured with a band pass filter, and the time series light intensity data were generated. The light detection region in the sample solution was rotated with the moving speed of 15 mm/second, BIN TIME was set to 10 μsec. and the measurement for 2 seconds was conducted 5 times. Then, similarly to the embodiment 1, after smoothing the time series light intensity data obtained by the measurements, the detection of the peak was done through the differentiation. Among the regions which could be regarded to be a pulse signal, the pulses which could be approximated with a gauss function and had the intensity of 1 or more were counted.

As shown in FIG. 14B, the pulse number increased with the increase of the target nucleic acid concentration. In particular, there is no overlapping in the standard deviations of the five measurements between the cases of 0M and 10 pM: This suggests that, according to the method of this embodiment, the measurement of the nucleic acid concentration of 10 pM or more is possible.

Thus, according to the above-mentioned inventive method, by moving, in a sample solution, the position of a micro region, i.e. a light detection region, namely scanning the inside of the sample solution and detecting individually a particle crossing the light detection region or conducting the counting of the particles, where no statistical procedures, such as calculation of fluorescence intensity fluctuation, performed in FCS, FIDA, etc., are included, it becomes possible to detect a condition or a characteristic of a particle to be observed in a sample solution whose concentration or number density of the particle to be observed is lower than the level used in FCS, FIDA, etc.

In this regard, since the inventive optical analysis technique basically uses the same optical system as FCS, FIDA, etc. it may be performed together with FCS, FIDA, etc. For example, in a case of detecting an interaction, etc. between two or more kinds of substances in a solution containing of these, when the concentration difference between substances is large, for example, when the concentration of one substance is nM order and that of the other substance is pM order, there can be conducted a manner that measurement and analysis are conducted by FCS or FIDA for the substance of the higher concentration while measurement and analysis are conducted by the inventive optical analysis technique for the substance of the lower concentration. In such a case, as illustrated in FIG. 1A, it is advantageous to prepare two or more photodetectors.

---

The invention claimed is:

1. An optical analysis method of detecting light from a light-emitting probe binding to a particle dispersed and moving at random in a sample solution to detect the particle by using an optical system of a confocal microscope or a multiphoton microscope, said method comprising steps of:
   preparing the sample solution containing the particle and the light-emitting probe;
   moving a position of a light detection region of the optical system in the sample solution by changing an optical path of the optical system;
   detecting light from the light detection region while moving the position of the light detection region in the sample solution, over a plurality of units of time;
   smoothing data values of light detected over the plurality of units of time, said smoothing being conducted until a gap in a light intensity variation over the plurality of units of time of a light signal from the light-emitting probe bound or having been previously bound to each particle can be disregarded; and
   detecting the particle individually based on smoothed data values by detecting, as a light signal of the particle, a light intensity variation over consecutive units among the plurality of units of time which has a predetermined profile which is expected from a single light-emitting probe moving relatively inside the light detection region, while disregarding a light intensity variation over consecutive units of time among the plurality of units of time which does not have the predetermined profile as noise.

2. The method of claim 1, further comprising a step of: counting the number of the individually detected particle(s) to count the number of the particle(s) detected during moving the position of the light detection region.

3. The method of claim 1, wherein, in the step of moving the position of the light detection region, the position of the light detection region is moved at a predetermined speed.

4. The method of claim 1, wherein, in the step of moving the position of the light detection region, the position of the light detection region is moved at a velocity quicker than a diffusional moving velocity of the light-emitting probe having bound to the particle.

5. The method of claim 1, wherein, in the step of detecting individually the light signal from the light-emitting probe having bound to each particle to detect individually the particle(s), the entering of one particle into the light detection region is detected based upon a shape of a time series light signal detected by the light detection portion.

6. The method of claim 1, wherein the step of preparing the sample solution comprises the step of separating the light-emitting probe having not bound to the particle from the sample solution.

7. The method of claim 1, wherein the step of preparing the sample solution comprises the step of making an acceptor which absorbs light from the light-emitting probe bind to the light-emitting probe having not bound to the particle.

8. The method of claim 1, wherein the light-emitting probe is a substance whose light-emitting characteristic changes when the light-emitting probe binds to the particle, and the detected light is light emitted from the light-emitting probe having bound to the particle.

9. The method of claim 1, wherein the light-emitting probe is a substance having an energy donor site and an energy acceptor site which cause a fluorescence energy transfer phenomenon when they are mutually close, wherein a distance of the energy donor site and the energy acceptor site is different between a condition where the substance has bound to the particle and a condition where the substance has not bound to the particle, and a wavelength characteristic of light emitted from the substance is different between a condition where the substance has bound to the particle and a condition where the substance has not bound to the particle; and that the detected light is light emitted from the light-emitting probe having bound to the particle.

10. The method of claim 1, wherein the light-emitting probe has an energy donor site and an energy acceptor site which cause a fluorescence energy transfer phenomenon; the step of preparing the sample solution includes the step of carrying out a reaction to decompose the light-emitting probe having bound to the particle; and the detected light is light emitted from the light-emitting probe decomposed through the reaction.

11. The method of claim 1, wherein the light-emitting probe is a probe pair comprising
   a first probe which is an energy donor in a fluorescence energy transfer phenomenon, and
   a second probe which is an energy acceptor in the fluorescence energy transfer phenomenon; and
   wherein the detected light is light of the second probe emitted through the fluorescence energy transfer phenomenon which occurs under a condition that both the first and second probes have bound to the particle.

12. The method of claim 1, wherein the particle has a site to be an energy acceptor of light emitted by the light-emitting probe; and the detected light is light emitted from the energy acceptor site of the particle through a fluorescence energy transfer phenomenon which occurs when the light-emitting probe binds to the particle.

13. The method of claim 1, wherein the particle has a light-emitting site; the light-emitting probe has a site to be an energy acceptor of the light which the light-emitting site of the particle emits; and the detected light is light emitted from the light-emitting probe through a fluorescence energy transfer phenomenon which occurs when the light-emitting probe binds to the particle.

14. The method of claim 1, wherein the particle is nucleic acid and the light-emitting probe is a nucleic acid binding protein.

15. The method of claim 1, wherein the light-emitting probe is a substance which consists of at least two components and emits fluorescence when the substance binds to the particle and the mutual position of the at least two components changes.

16. The method of claim 1, wherein the predetermined profile which is expected from a single light-emitting probe moving relatively inside the light detection region has an approximately bell shape.

17. The method of claim 1,
wherein, after the smoothing of the data values, a pulse existing region is determined by referring to the time differential value sequentially, and
wherein after the pulse existing region is determined, an individual particle is detected by fitting the predetermined profile to the smoothed data values in the pulse existing region.

* * * * *

SEQUENCE LISTING

<160> NUMBER OF SEQ ID NOS: 15

<210> SEQ ID NO 1
<211> LENGTH: 28
<212> TYPE: DNA
<213> ORGANISM: Artificial
<220> FEATURE:
<223> OTHER INFORMATION: forming a molecular beacon

<400> SEQUENCE: 1
cctacgccaa cagctccaac tacgtagg                                      28

<210> SEQ ID NO 2
<211> LENGTH: 54
<212> TYPE: DNA
<213> ORGANISM: Artificial
<220> FEATURE:
<223> OTHER INFORMATION: including a site which binds to a molecular
      beacon

<400> SEQUENCE: 2
gtagttggag ctgttggcgt aggcaagagt gccttgacga tacagctaat tcag         54

<210> SEQ ID NO 3
<211> LENGTH: 100
<212> TYPE: DNA
<213> ORGANISM: Artificial
<220> FEATURE:
<223> OTHER INFORMATION: For testing the effect of scanning molecular
      counting method

<400> SEQUENCE: 3
gaaacagcta tgaccatgat tacgccaagc ttgcatgcct gcaggtcgac tctagaggat    60
ccccgggtac cgagctcgaa ttcactggcc gtcgttttac                         100

<210> SEQ ID NO 4
<211> LENGTH: 21
<212> TYPE: DNA
<213> ORGANISM: Artificial
<220> FEATURE:

```
<223> OTHER INFORMATION: For a fluorescent probe in scanning molecule
      counting method

<400> SEQUENCE: 4
ggggatcctc tagagtcgac c                                            21

<210> SEQ ID NO 5
<211> LENGTH: 20
<212> TYPE: DNA
<213> ORGANISM: Artificial
<220> FEATURE:
<223> OTHER INFORMATION: For a fluorescent donner probe in scanning
      molecule counting method

<400> SEQUENCE: 5
cctacgccac cagctccaac                                              20

<210> SEQ ID NO 6
<211> LENGTH: 20
<212> TYPE: DNA
<213> ORGANISM: Artificial
<220> FEATURE:
<223> OTHER INFORMATION: For a fluorescent accepter probe in scanning
      molecule counting method

<400> SEQUENCE: 6
agctgtatcg tcaaggcact                                              20

<210> SEQ ID NO 7
<211> LENGTH: 17
<212> TYPE: DNA
<213> ORGANISM: Artificial
<220> FEATURE:
<223> OTHER INFORMATION: For a fluorescent donner quenching probe

<400> SEQUENCE: 7
ggagctggtg gcgtagg                                                 17

<210> SEQ ID NO 8
<211> LENGTH: 17
<212> TYPE: DNA
<213> ORGANISM: Artificial
<220> FEATURE:
<223> OTHER INFORMATION: For a fluorescent accepter quenching probe

<400> SEQUENCE: 8
agtgccttga cgataca                                                 17

<210> SEQ ID NO 9
<211> LENGTH: 78
<212> TYPE: DNA
<213> ORGANISM: Artificial
<220> FEATURE:
<223> OTHER INFORMATION: For testing the effect of scanning molecule
      counting method

<400> SEQUENCE: 9
atgactgaat ataaacttgt ggtagttgga gctggtggcg taggcaagag tgccttgacg   60
atacagctaa ttcagaat                                                78

<210> SEQ ID NO 10
<211> LENGTH: 32
<212> TYPE: DNA
<213> ORGANISM: Artificial
<220> FEATURE:
<223> OTHER INFORMATION: used for a fluorescent probe
```

-continued

<400> SEQUENCE: 10
aaacttgtgg tagttggagc tgttggcgta gg     32

<210> SEQ ID NO 11
<211> LENGTH: 24
<212> TYPE: DNA
<213> ORGANISM: Artificial
<220> FEATURE:
<223> OTHER INFORMATION: used for a quenching probe

<400> SEQUENCE: 11
aacagctcca actaccacaa gttt     24

<210> SEQ ID NO 12
<211> LENGTH: 494
<212> TYPE: DNA
<213> ORGANISM: Artificial
<220> FEATURE:
<223> OTHER INFORMATION: for testing scanning molecule counting method

<400> SEQUENCE: 12
gaagtacagt tcattacgat acacgtctgc agtcaactgg aattttcatg attgaatttt     60
gtaaggtatt ttgaaataat ttttcatata aggtgagtt tgtattaaaa ggtactggtg     120
gagtatttga tagtgtatta accttatgtg tgacatgttc taatatagtc acattttcat     180
tatttttatt ataaggcctg ctgaaaatga ctgaatataa acttgtggta gttggagctg     240
gtggcgtagg caagagtgcc ttgacgatac agctaattca gaatcatttt gtggacgaat     300
atgatccaac aatagaggta aatcttgttt taatatgcat attactggtg caggaccatt     360
ctttgataca gataaaggtt tctctgacca ttttcatgag tacttattac aagataatta     420
tgctgaaagt taagttatct gaaatgtacc ttgggtttca agttatatgt aaccattaat     480
atgggaactt tact     494

<210> SEQ ID NO 13
<211> LENGTH: 25
<212> TYPE: DNA
<213> ORGANISM: Artificial
<220> FEATURE:
<223> OTHER INFORMATION: used for an E probe in QUAL reaction

<400> SEQUENCE: 13
tcttgcctac gccaccagct ccaac     25

<210> SEQ ID NO 14
<211> LENGTH: 28
<212> TYPE: DNA
<213> ORGANISM: Artificial
<220> FEATURE:
<223> OTHER INFORMATION: used for an N probe in QUAL reaction

<400> SEQUENCE: 14
ttctgaatta gctgtatcgt caaggcac     28

<210> SEQ ID NO 15
<211> LENGTH: 53
<212> TYPE: DNA
<213> ORGANISM: Artificial
<220> FEATURE:
<223> OTHER INFORMATION: used for a target molecule in QUAL Reaction

```
<400> SEQUENCE: 15
gttggagctg gtggcgtagg caagagtgcc ttgacgatac agctaattca gaa          53
```